United States Patent [19]

Kamiya et al.

[11] 4,324,892
[45] Apr. 13, 1982

[54] 7-(N-SUBSTITUTED-2-PHENYL-GLYCINAMIDO)-3-SUBSTITUTED-3-CEPHEM-4-CARBOXYLIC ACID COMPOUNDS

[75] Inventors: Takashi Kamiya, Suita; Tsutomu Teraji, Toyonaka; Keiji Hemmi, Kyoto; Jiro Goto, Mino, all of Japan

[73] Assignee: Fujisawa Pharmaceutical Co., Ltd., Osaka, Japan

[21] Appl. No.: 45,011

[22] Filed: Jun. 4, 1979

Related U.S. Application Data

[62] Division of Ser. No. 824,910, Aug. 15, 1977, Pat. No. 4,172,198.

[30] Foreign Application Priority Data

Aug. 17, 1976 [GB] United Kingdom ............. 34302/76
Nov. 29, 1976 [GB] United Kingdom ............. 49748/76

[51] Int. Cl.³ .................. C07D 501/46; C07D 501/34
[52] U.S. Cl. ......................................... 544/28; 544/22
[58] Field of Search ............................... 544/22, 27, 28

[56] References Cited

U.S. PATENT DOCUMENTS

| | | | |
|---|---|---|---|
| 3,769,281 | 10/1973 | Chauvette | 544/27 X |
| 3,867,380 | 2/1975 | Dunn et al. | 544/26 |
| 3,985,740 | 10/1976 | Essery et al. | 544/27 |
| 4,015,000 | 3/1977 | Kocsis et al. | 544/27 X |
| 4,036,834 | 7/1977 | Murakami et al. | 544/27 |
| 4,039,536 | 8/1977 | Takano et al. | 544/27 |
| 4,041,161 | 8/1977 | Kocsis et al. | 544/27 X |
| 4,048,161 | 9/1977 | Lunn et al. | 544/27 |
| 4,053,470 | 10/1977 | Doub et al. | 544/28 X |
| 4,058,610 | 11/1977 | Cox et al. | 544/26 X |
| 4,064,241 | 12/1977 | Ross et al. | 544/27 X |
| 4,068,074 | 1/1978 | Murakami et al. | 544/27 |
| 4,103,008 | 7/1978 | Toshiyasu et al. | 544/28 X |
| 4,107,304 | 8/1978 | Schröck et al. | 544/28 X |
| 4,110,327 | 8/1978 | Saikawa et al. | 544/28 X |
| 4,154,831 | 5/1979 | Kocsis et al. | 544/27 X |
| 4,156,724 | 5/1979 | Yamada et al. | 544/27 X |
| 4,165,373 | 8/1979 | Yamada et al. | 544/27 X |

FOREIGN PATENT DOCUMENTS

| | | | |
|---|---|---|---|
| 50-151895 | 12/1975 | Japan | 544/28 |
| 50-157387 | 12/1975 | Japan | 544/28 |
| 606016 | 10/1978 | Switzerland | 544/22 |

Primary Examiner—Donald G. Daus
Assistant Examiner—Diana G. Rivers
Attorney, Agent, or Firm—Dayton R. Stemple, Jr.

[57] ABSTRACT

New cephalosporin compounds of the formula:

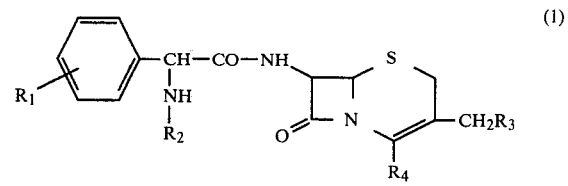

wherein $R_1$ is hydrogen or hydroxy, $R_2$ is a substituted alkanoyl group, $R_3$ is hydrogen, carbamoyloxy, alkanoyloxy or a heterocyclic-thio group which may have suitable substituents, and $R_4$ is carboxy or protected carboxy.

5 Claims, No Drawings

7-(N-SUBSTITUTED-2-PHENYLGLYCINAMIDO)-3-SUBSTITUTED-3-CEPHEM-4-CARBOXYLIC ACID COMPOUNDS

This is a division, of application Ser. No. 824,910, filed Aug. 15, 1977 now U.S. Pat. No. 4,172,198.

This invention relates to new cephalosporin compounds which possess antibacterial activity and preparation thereof.

Hitherto, many antibiotic cephalosporin compounds have been prepared and only a few of them are used therapeutically. According to this invention, there are provided new cephalosporin compounds which show remarkable antimicrobial activity against a number of pathogenic Gram-negative and Gram-positive bacteria, and especially against cephalosporin-resistant strains.

The new cephalosporin compounds of this invention include 7-(N-substituted-2-phenylglycinamido)-3-substituted-3-cephem-4-carboxylic acid compounds represented by the following structural formula:

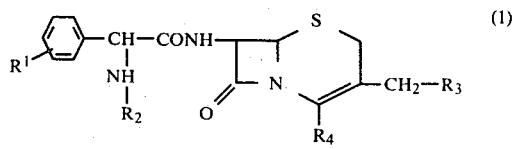

wherein
$R_1$ is hydrogen or hydroxy,
$R_2$ is a substituted alkanoyl group, in which the substituent on the alkanoyl group is thienyl; phthalimido; hydroxy- or oxopyrido[1,2-a] pyrimidinyl;

a 5-membered heterocyclic group containing two or three hetero atoms selected from N, O and S, which has one or two substituents selected from hydroxy, oxo, alkyl, phenyl, halophenyl, amino, N',N'-dialkylaminoalkylideneamino, imino, mercapto, thioxo and alkylthio;

a 5-membered heterocyclic group containing four hetero atoms selected from N, O and S, which may be substituted with amino or N',N'-dialkylaminoalkylideneamino;

a 6-membered heterocyclic group containing two or three hetero atoms selected from N, O and S, which has one or two substituents selected from hydroxy, oxo, alkyl, amino, N',N'-dialkylaminoalkylideneamino, imino, mercapto, thioxo, alkylthio, halogen and carboxy;

provided that when said 6-membered heterocyclic group is 1,2,4-triazinyl substituted with two substituents, one of said substituents is a group other than hydroxy or oxo;

or a group of the formula: —A—$R_5$ wherein A is O or S and $R_5$ is a 5 or 6 membered heterocyclic group containing at least one of hetero atom selected from N, O and S, which may be substituted with at least one of hydroxy, oxo, mercapto, thioxo, alkyl, halogen, hydroxyalkyl and haloalkyl, $R_3$ is hydrogen, carbamoyloxy, alkanoyloxy or a heterocyclic-thio group which may have suitable substituent(s), and $R_4$ is carboxy or a protected carboxy group, provided that $R_2$ is a group of the formula:
—A—$R_5$ (wherein A and $R_5$ are each as defined above), when $R_3$ is alkanoyloxy or $R_2$ is alkanoyl substituted with pyridyl, $R_3$ is hydrogen and $R_1$ and $R_4$ are each as defined above, and a salt thereof.

Accordingly, it is one object of the present invention to provide the new 7-(N-substituted-2-phenylglycinamido)-3-substituted-3-cephem-4-carboxylic acid compound (1) and a salt thereof, which are active against a number of pathogenic microorganisms.

Another object of the present invention is to provide processes for the preparation of said cephalosporin compounds.

A further object of the present invention is to provide pharmaceutical composition comprising, an effective antimicrobial agents, said cephalosporin compounds for the treatment of infectious disease caused by various pathogenic bacteria in human being and animals.

The terms used with regard to the definitions of the symbols in the structural formula (1), and other formulae described throughout this specification and the claims are explained as follows:

The alkanoyl group of the substituted alkanoyl group and alkanoyl moiety, mean, preferably, lower alkanoyl such as formyl, acetyl, propionyl, butyryl, isobutyryl, valeryl, isovaleryl or pivaloyl.

The 5-membered heterocyclic group containing two or three hetero atoms selected from N, O and S can be illustrated by suitable examples as given below: an aromatic one such as triazolyl (e.g. 1H-1,2,3-triazolyl, 2H-1,2,3-triazolyl, 1H-1,2,4-triazolyl or 4H-1,2,4-triazolyl), oxazolyl, isoxazolyl, oxadiazolyl (e.g. 1,2,4-oxadiazolyl, 1,3,4-oxadiazolyl or furazanyl), thiazolyl, isothiazolyl, thiadiazolyl (e.g. 1,2,4-thiadiazolyl, 1,2,5-thiadiazolyl or 1,3,4-thiadiazolyl), etc. and a partially or fully saturated one of said aromatic one, such as triazolinyl (e.g. 1,2,3-triazolinyl or 1,2,4-triazolinyl), triazolidinyl(1,2,3-triazolidinyl or 1,2,4-triazolidinyl), 2,3 or 4-oxazolinyl, oxazolidinyl, 2,3 or 4-isoxazolinyl, isoxazolidinyl, oxadiazolinyl (e.g. 1,2,4-oxadiazolin-, 1,3,4-oxadiazolin- or 1,2,5-oxadiazolin- 2,3 or 4-yl), oxadiazolidinyl (e.g. 1,2,4-oxadiazolidinyl, 1,3,4-oxadiazolidinyl or 1,2,5-oxadiazolidinyl), 2,3 or 4-thiazolinyl, thiazolidinyl, 2,3 or 4-isothiazolinyl, isothiazolidinyl, thiadiazolinyl (e.g. 1,2,4-thiadiazolin-, 1,2,5-thiadiazolin- or 1,3,4-thiadiazolin-2,3 or 4-yl), thiadiazolidinyl (e.g. 1,2,4-thiadiazolidinyl, 1,2,5-thiadiazolidinyl or 1,3,4-thiadiazolidinyl), etc., which has one or two substituents selected from hydroxy, oxo, alkyl, phenyl, halophenyl, amino, N',N'-dialkylaminoalkylideneamino, imino, mercapto, thioxo and alkylthio.

The 5-membered heterocyclic group containing four hetero atoms selected from N, O and S can be illustrated by suitable examples as given below: an aromatic one such as tetrazolyl (e.g. 1H-tetrazolyl or 2H-tetrazolyl), which may be substituted with amino or N',N'-dialkylaminoalkylideneamino.

The 6-membered heterocyclic group containing two or three hetero atoms selected from N, O and S, can be illustrated by suitable examples as given below: aromatic one such as triazinyl (e.g. 1,3,5-triazinyl or 1,2,4-triazinyl), pyrimidinyl, pyridazinyl, pyrazinyl, etc.; a partially or fully saturated one of the said aromatic one, such as 1,2-dihydro-1,3,5-triazinyl, 1,2,3,4-tetrahydropyrimidinyl, 2,3-dihydropyridazinyl, piperazinyl, etc.; or thiadiazinyl (e.g. 2H-1,2,4-thiadiazinyl, 4H-1,2,4-thiadiazinyl, 2H-1,3,4-thiadiazinyl, 4H-1,3,4-thiadiazinyl or 2H-1,3,5-thiadiazinyl), pyranyl (e.g. 2H-pyranyl or 4H-pyranyl), thiomorpholino, etc., which has one or two substituents selected from hydroxy, oxo, alkyl, amino, N',N'-dialkylaminoalkylideneamino, imino, mercapto, thioxo, alkylthio, halogen and carboxy.

The 5 or 6 membered heterocyclic group containing at least one hetero atom selected from N, O and S are, preferably one such as pyrrolyl, pyrrolinyl, imidazolyl, pyrazolyl, pyridyl, 1,4-dihydropyridyl, pyrimidinyl, pyrazinyl, pyridazinyl, triazolyl, tetrazolyl, furyl, pyranyl, oxazolyl, isoxazolyl, oxadiazolyl, thiazolyl or thiadiazolyl, and more preferable examples are given below: aromatic one such as triazolyl (e.g. 1H-1,2,3-triazolyl, 2H-1,2,3-triazolyl, 1H-1,2,4-triazolyl or 4H-1,2,4-triazolyl), thiadiazolyl (e.g. 1,2,4-thiadiazolyl, 1,2,5-thiadiazolyl or 1,3,4-thiadiazolyl), pyridyl, pyrimidinyl, pyrazinyl, pyridazinyl, etc. or a partially or fully saturated one of said aromatic one such as 1,4-dihydropyridyl, 2,3,4,5-tetrahydropyrimidinyl, 1,4-dihydropyrimidinyl, 1,2-dihydropyrazinyl, etc., or pyranyl (e.g. 2H-pyranyl or 4H-pyranyl), etc., which may be substituted with at least one of hydroxy, oxo, thioxo, mercapto, alkyl, halogen, hydroxyalkyl and haloalkyl.

The alkyl and alkyl moieties are monovalent radicals of a straight or branched and saturated hydrocarbon, preferably lower ones such as methyl, ethyl, propyl, isopropyl, butyl, isobuyl, t-butyl, pentyl, neo-pentyl, hexyl, heptyl or octyl.

The alkylthio is one which has the alkyl moiety mentioned above and preferably lower alkylthio such as methylthio, ethylthio, propylthio, isopropylthio, butylthio, isobutylthio, t-butylthio, pentylthio, neo-pentylthio, hexylthio, heptylthio or octylthio.

The halogen and halo-moiety are fluorine, chlorine, bromine or iodine.

The haloalkyl is one which has the halo-moiety and the alkyl moiety as mentioned above, and preferably halo(lower) alkyl such as mono-halo(lower)alkyl (e.g. chloromethyl, bromomethyl or chloropropyl), di-halo(-lower)alkyl (e.g. 1,2-dichloroethyl, 1,2-dibromoethyl or 2,2-dichloroethyl) or tri-halo(lower)alkyl (e.g. trifluoromethyl or 1,2,2-trichloroethyl).

The halophenyl is one which has the halomoiety as mentioned above, such as chlorophenyl, dichlorophenyl or bromophenyl.

The N',N'-di-alkylaminoalkylideneamino is preferably N',N'-di(lower)alkylamino(lower)alkylideneamino such as N',N'-dimethylaminomethyleneamino, N',N'-diethylaminomethyleneamino or N',N'-di-methylaminoethylideneamino.

The alkylene is bivalent radical of a straight or branched and saturated hydrocarbon, preferably lower one such as methylene, methylmethylene, ethylene, trimethylene, propylene, dimethylmethylene, or tetramethylene.

The hydroxyalkyl is preferably hydroxy(lower)alkyl such as hydroxymethyl, 1 or 2-hydroxyethyl, 1,2 or 3-hydroxypropyl or 1-hydroxyisopropyl.

The heterocyclic-thio group includes one conventionally employed in cephalosporin field as a substituent on the 3-methyl group, and said heterocyclic moiety are prefeably exemplified with N-containing heterocyclic group such as unsaturated 3 to 8-membered heteromonocyclic group containing 1 to 4 nitrogen atom(s) (e.g. pyrrolyl, pyrrolinyl, imidazolyl, pyrazolyl, pyridyl and its N-oxide, pyrimidinyl, pyrazinyl, pyridazinyl, triazolyl or tetrazolyl); saturated 3 to 8-membered heteromonocyclic group containing 1 to 4 nitrogen atom(s) (e.g. pyrrolidinyl, imidazolidinyl, piperidino or piperazinyl); unsaturated condensed heterocyclic group containing 1 to 4 nitrogen atom(s) (e.g. indolyl, isoindolyl, indolizynyl, benzimidazolyl, quinolyl, isoquinolyl, indazolyl or benzotriazolyl); unsaturated 3 to 8-membered heteromonocyclic group containing 1 to 2 oxygen atom(s) and 1 to 3 nitrogen atom(s) (e.g. oxazolyl, isoxazolyl or oxadiazolyl); saturated 3 to 8-membered heteromonocyclic group containing 1 to 2 oxygen atom(s) and 1 to 3 nitrogen atom(s) (e.g. morpholinyl); unsaturated condensed heterocyclic group containing 1 to 2 oxygen atom(s) and 1 to 3 nitrogen atom(s) (e.g. benzoxazolyl or benzoxadiazolyl); unsaturated 3 to 8-membered heteromonocyclic group containing 1 to 2 sulfur atom(s) and 1 to 3 nitrogen atom(s) (e.g. thiazolyl or thiadiazolyl); saturated 3 to 8-membered heteromonocyclic group containing 1 to 2 sulfur atom(s) and 1 to 3 nitrogen atom(s) (e.g. thiazolidinyl); unsaturated condensed heterocyclic group containing 1 to 2 sulfur atom(s) and 1 to 3 nitrogen atom(s) (e.g. benzothiazolyl or benzothiadiazolyl) and the like, wherein said heterocyclic moiety may have at least one suitable substituent(s) such as alkyl as illustrated above: alkenyl; ary; halogen as illustrated above; amino; imino; aminoalky; acylaminoalkyl; mono- or di-alkylaminoalkyl; carboxyalkyl and the like.

The alkenyl is a monovalent radical of a straight or branched hydrocarbon which contains one or more double bond(s), and preferably lower alkenyl such as vinyl, allyl, butenyl, butanedienyl or penta-2,4-dienyl.

The aryl is, for example, phenyl, tolyl or xylyl.

The aminoalkyl is preferably amino(lower)alkyl such as aminomethyl, aminoethyl, aminopropyl, aminobutyl or aminohexyl.

The acylaminoalkyl is a N-acylated aminoalkyl group, and suitable examples of the acyl moiety are alkanoyl as mentioned above, aroyl such as benzoyl or toluoyl, aralkanoyl which is alkanoyl substituted with above mentioned aryl group, such as 2-phenylacethyl or 3-phenylpropionyl, or an organic sulfonyl (e.g. mesyl or tosyl).

The preferable examples of acylaminoalkyl are lower alkanamido(lower)alkyl such as acetamidomethyl, propionamidomethyl or acetamidoethyl; aroylamido(lower)alkyl such as benzamidomethyl or toluoylaminomethyl; and ar(lower)alkanamido(lower)alkyl such as (2-phenylacetamido)methyl or (3-phenylpropionamido)methyl.

The preferable examples of mono- or di-alkylaminoalkyl are mono- or di-(lower)alkylamino(lower)alkyl wherein the lower alkyl moieties are illustrated above, such as methylaminomethyl, methylaminoethyl, ethylaminomethyl, ethylaminoethyl, dimethylaminomethyl, diethylaminomethyl, diethylaminoethyl, dimethylaminoethyl, dimethylaminopropyl, methylaminopropyl, or diethylaminopropyl.

The preferable examples of carboxyalkyl are carboxy(lower)alkyl such as carboxymethyl, carboxyethyl or carboxypropyl.

The protected carboxy group means a group wherein the carboxy group at the compound (1) is modified, whereby the compound (1) can exhibit pharmaceutically more effective properties, for example, better absorption in oral administration and, for this purpose, there are conventionally employed esters in this field. Suitable ester moieties for oral administration are acyloxyalkyl (preferably 1-acyloxyalkyl) which has the acyl and alkyl moieties as mentioned above and, preferably alkanoyloxyalkyl such as acetoxymethyl, 1-acetoxyethyl, 1-propionylmethyl, butynyloxymethyl or valeryloxymethyl; aroyloxyalkyl such as benzoyloxymethyl or 1-benzoylethyl; and 1-aralkanoyloxyalkyl such as 2-phenylacetoxymethyl or 1-(2-phenylacetoxy)ethyl, and further esters in which the oxygen atom of the acyloxyalkyl is replaced with nitrogen or sulfur atom (i.e. acylamidoalkyl ester or acylthioalkyl ester), and an ester of isobenzofuran-1-ylmethyl is also effective for oral use, and, in addition to the above esters, there can be included the following usual esters mentioned below in the scope of the protected carboxy group of this invention: alkyl ester (e.g., methyl ester, ethyl ester, propyl ester, isopropyl ester, butyl ester, isobutyl ester, tert-butyl ester, tert-pentyl ester or hexyl ester, alkanesulfonyl(lower)alkyl ester (e.g., 2-mesylethyl ester or 3-mesylpropyl ester), mono(or di or tri) haloalkyl ester (e.g., trichloromethyl ester, 2-iodoethyl ester or 2,2,2-trichloroethyl ester), aralkyl ester which may have at least one suitable substituent(s) [e.g., benzyl ester, 4-methoxybenzyl ester, 4-nitrobenzyl ester, phenethyl ester, trityl ester, diphenylmethyl ester, bis-(methoxyphenyl)methyl ester, 3,4-dimethoxybenzyl ester or 4-hydroxy-3,5-di-tert-butylbenzyl ester], aroylalkyl ester (e.g., phenacyl ester or toluoylmethyl ester), alkoxyalkyl ester (e.g., methoxymethyl ester or ethoxymethyl ester), alkanoylalkyl ester (e.g., acetonyl ester or propionylmethyl ester), cycloalkylalkyl ester (e.g., 1-cyclopropylethyl ester or 2-cyclopropylpropyl ester), alkenyl ester (e.g., allyl ester or isopropenyl), alkynyl ester (e.g., ethynyl ester or propynyl ester), aryl ester which may have at least one suitable substituent(s) (e.g. phenyl ester, p-nitrophenyl ester, p-chlorophenyl ester, tolyl ester, tert-butyl phenyl ester, xylyl ester, mesityl ester or cumenyl ester), an ester with silyl compound, such as methyldichlorosilyl ester, chlorodimethylsilyl ester, trimethylsilyl ester, triethylsilyl ester, methyldiethylsilyl ester, methoxydichlorosilyl ester, chlorodiethoxysilyl ester, methyldiethoxysilyl ester or tri(2-chloroethoxy)silyl ester, and the like.

The term "lower" used in connection with an aliphatichydrocarbon moiety such as alkyl, alkenyl, alkynyl, alkylene or alkylidene is intended to mean the one having 1 to 8 carbon atom(s), preferably 1 to 6 carbon atom(s).

Salts of the compound (1) include the salts at carboxy function or amino function and inner salt thereof. Salts at the carboxy are, for example, salts with an alkali metal such as sodium or potassium, an alkakine earth metal such as calcium or magnesium, ammonia, an organic base such as diethylamine, triethylamine, trimethylamine, pyridine, dimethylaniline, ethanolamine, diethanolamine, triethanolamine, dicyclohexylamine, piperazine or N-methylmorpholine and a basic amino acid such as lysine or arginine. Salts at the amino are, for example, salts with an inorganic acid such as hydrochloric acid, hyrobromic acid, sulfuric acid or phosphoric acid, an organic acid such as formic acid, acetic acid, oxalic acid, lactic acid, tartaric acid, maleic acid, glutaric acid or palmitic acid. an acidic aminoacid such as aspartic acid or glutamic acid and like.

According to the present invention, the compound (1) can be produced by various processes fall into the following classification:

Process 1

This process comprises reacting a compound of the formula:

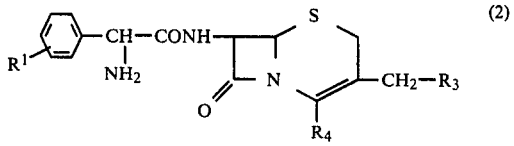

wherein $R_1$, $R_3$ and $R_4$ are each as defined above, or its reactive derivative at the amino group or a salt thereof, with a corboxylic acid of the formula:

wherein $R_2$ is as defined above, or its salt or reactive derivative at the carboxy group to give the compound (1) or its salt, Suitable reactive derivative at the amino group of the starting compound (2) may include isocyanato, isothiocyanato, or Schiff's base or its tautomeric enamine type isomer formed by the reaction of the amino group with an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g., acetone, methyl ethyl ketone, methyl isobutyl ketone, acetylacetone, ethyl acetoacetate, etc.), a silyl derivative formed by the reaction of the compound (2) with a conventional silyl compound such as bis(trimethylsilyl)acetamide or the like, a derivative formed by reaction of the compound (2) with phosphorus trichloride or phosgene, and the like.

In this reaction, the compound (2) may be reacted with an excess silyl compound to form a silyl derivative of the compound (2) at the carboxy group or the amino and carboxy groups, in advance of subjecting to the reaction with the compound (3) or its reactive derivatives at the carboxy group or salts thereof, and this is also included in the scope of the present reaction.

Examples of the salt of the compound (2) can be referred to that of the object compound (1) as illustrated above.

Suitable reactive derivative at the carboxy group of another starting compound (3) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid or halogenated phosphoric acid), dialkylphosphorus acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid) or aromatic carboxylic acid (e.g. benzoic acid); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethylimmoniomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester or 8-quinolyl thioester), or an ester with N,N-dimethylhydroxylamine, 1-hydroxy-2-(1H)- pyridone, N-hydroxysuccinimide, N-hydroxyphthalimide or 1-hydroxy-6-chloro-1H-benzotriazole, and the like. These reactive derivatives can be optionally selected from them according to the kind of the compound (3) to be used.

The salt of the compound (3) is preferably a salt with an inorganic base such as sodium potassium or calcium, or an organic base such as triethylamine or pyridine.

The reaction is usually carried out in a conventional solvent such as water, acetone, dioxane, acetonitrile, chloroform, methylene chloride, ethylene chloride, tetrahydrofuran, ethyl acetate, N,N-dimethyl formamide, pyridine or any other organic solvent which does not adversely influence to the reaction. Amoung these solvents, hydrophilic solvents may be used in a mixture with water.

When the compound (3) is used in free acid form or its salt form in the reaction, the reaction is preferably carried out in the presence of a conventional condensing agent such as N,N'-dicyclohexycarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intramolecular salt, (chloromethylene) dimethylammonium chloride, 1-(p-chlorobenzenesulfonyloxy)-6-chloro-1H-benzotriazole, a Vilsmeier reagent which is, for example, prepared by the reaction of dimethylformamide with thionyl chloride, phosgen, oxalyl chloride or phosphorus pentachloride, or the like.

The reaction may be also carried out in the presence of an inorganic or organic base such as an alkali metal bicarbonate, an alkali metal hydroxide, an alkaline earth metal hydroxide, alkali metal(lower)alkoxide, tri(lower)alkylamine, pyridine, N-(lower)alkylmorphorine, N,N-di(lower)alkylbenzylamine, or the like. The reaction temperature is not critical, and the reaction is usually carried out under cooling or at room temperature.

In case that this reaction is carried out in the presence of a Vilsmeier reagent as mentioned above with the compound (3) wherein $R_2$ is alkanoyl substituted with the 5 or 6-membered heterocyclic group bearing amino function, there may be occasionally produced the compound (1-5) which is defined in the following process 5. And thus produced compound (1-5) may be converted to the corresponding free-amino compound (1-4) which is also defined in the following process 5, by removing the N',N'-di-alkylaminoalkylidene group off, as exemplified in the following process 5 or, in some occasion, during the post-treatment of the reaction mixture for isolation and/or purification of the compound (1-5).

The starting compound (3) wherein $R_2$ is an alkanoyl substituted with a group of the formula: -A-$R_5$ (in which A and $R_5$ are each as defined above) is novel, and among them the novel compound representable by the following formula:

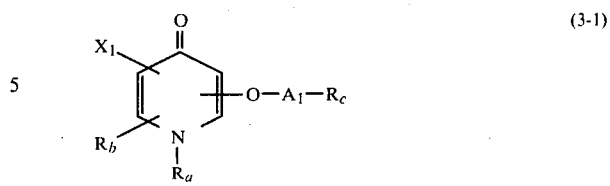

wherein
$R_a$ is hydrogen or alkyl
$R_b$ is hydrogen, alkyl, haloalkyl or hydroxyalkyl,
$R_c$ is carboxy or protected carboxy,
$A_1$ is alkylene and
$X_1$ is hydrogen or halogen,
can be prepared according to the following processes:

(Process i)

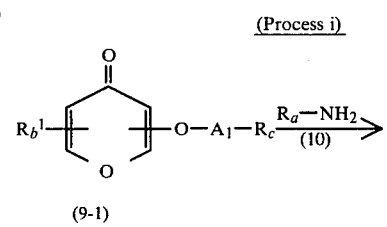

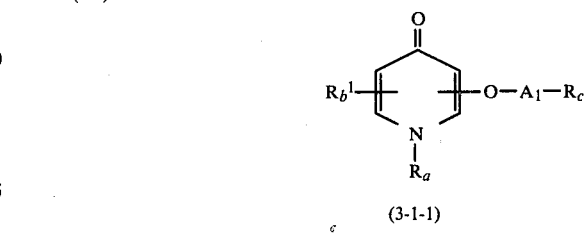

wherein $R_a$, $R_c$ and $A_1$ are each as defined above and $Rb^1$ is hydrogen, alkyl or hydroxyalkyl.

(Process ii)

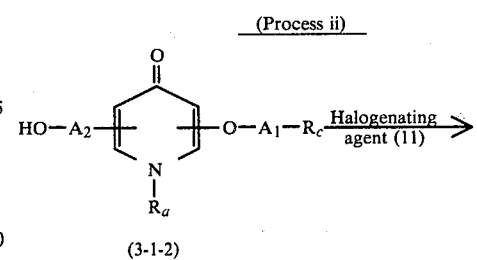

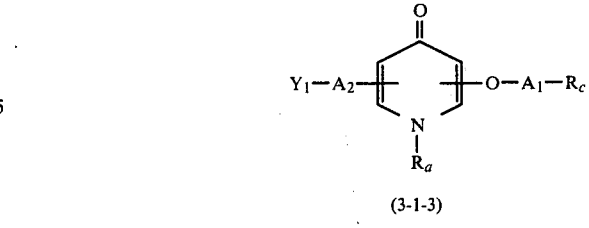

wherein $R_a$, $R_c$ and $A_1$ are each as defined above and $A_2$ is alkylene and $Y_1$ is halogen.

Suitable halogenating agent (11) includes a conventional one which is used for the transformation of hydroxy group into halogen atom, such as thionyl chloride, phosphorus tribromide or phosphorus pentachloride.

(Process iii)

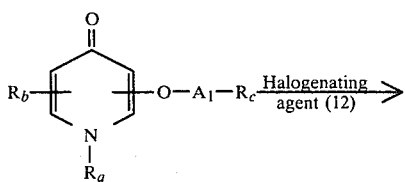

(3-1-4)

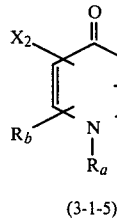

(3-1-5)

wherein $R_a$, $R_b$, $R_c$ and $A_1$ are each as defined above, and $X_2$ is halogen.

A suitable halogenating agent (12) includes a conventional one which is used for subtitution of hydrogen atom with halogen atom, such as halogen, N-haloimide (e.g. N-chlorosuccinimide, N-bromosuccinimide, N-bromophthalimide), sodium hypochloraite or trichloroisocyanuric acid.

(Process iv)

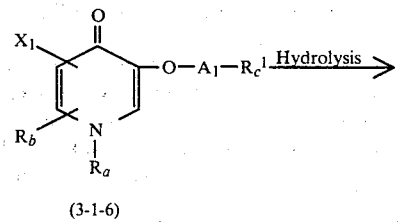

(3-1-6)

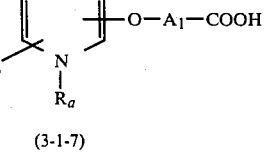

(3-1-7)

wherein $R_a$, $R_b$, $A_1$ and $X_1$ are each as defined above and $R_c^1$ is protected carboxy.

A compound of the formula:

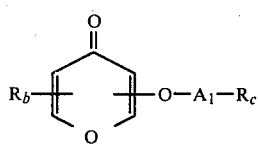

(9)

wherein $R_b$, $R_c$ and $A_1$ are each as defined above, which includes the compound (9-1) used as the starting compound in Process i, can be prepared by reacting a compound of the formula:

$$\text{(9-2)}$$

wherein $R_b$ is as defined above, with a compound of the formula:

$$Y_2\text{-}A_1\text{-}R_c \quad (13)$$

wherein $R_c$ and $A_1$ are each as defined above and $Y_2$ is a residue of an acid such as hydrochloric acid, hydroiodic acid, hydrobromic acid, sulfuric acid, alkanesulfonic acid or toluenesulfonic acid.

The compounds (9) and (3-1-4) wherein $R_b$ is alkyl, can be prepared by reducing those compounds wherein $R_b$ is haloalkyl. In this reaction, there may be employed any conventional reduction used for replacement of halogen atom to hydrogen atom, such as reduction using an acid and a metal or catalytic reduction.

And further, the new starting compound (3) other than 4-oxo-1,4-dihydropyridine compounds as mentioned above, can be prepared by analogous and/or conventional methods well known in the art for the preparation of known analogous compounds.

Process 2

This process comprises reacting a compound of the formula:

$$\text{(4)}$$

wherein $R_3$ and $R_4$ are each as defined above, or its reactive derivative at the amino group or a salt thereof, with a N-substituted phenylglycine compound of the formula:

$$\text{(5)}$$

wherein $R_1$ and $R_2$ are each as defined above, or its salt or reactive derivative at the carboxy group to give the compound (1) or its salt, The starting compound (5) can be prepared by reacting a compound of the formula:

$$\text{(6)}$$

wherein $R_1$ is as defined above, or its reactive derivative at the amino group or a salt thereof, with the carboxylic acid (3) or its salt or reactive derivative at the carboxy group.

Examples of the reactive derivative at the amino group and salt of the compounds (4) and (6) can be referred to those of the compound (2), and also the salt and reactive derivative at the carboxy group of the compound (5) can be referred to those of the compounds (2) and (3) as illustrated in the process 1, respectively.

The reactions for the preparation of the starting compound (5) by reacting the compound (6) with the compound (3) and for this process 2 can be also referred to and can be carried out in the substantially same manner as that of the process 1.

Process 3

Among the object compound (1), some compounds of the formula:

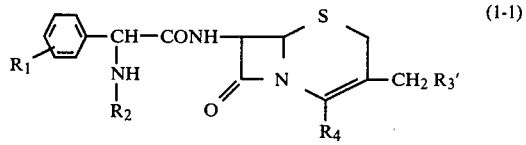
(1-1)

wherein $R_1$ and $R_4$ are each as defined above and $R_2$ is an alkanoyl substituted with a group of the formula: $-A-R_5$ (wherein A and $R_5$ are each as defined above) and $R_3'$ is a heterocyclic-thio group which may have suitable substituent(s), can be prepared by process 3 which comprises reacting a compound of the formula:

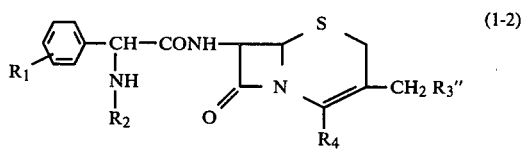
(1-2)

wherein $R_1$ and $R_4$ are each as defined above, and $R_2$ is defined in the formula (1-1) and $R_3''$ is a conventional group which is capable to be replaced by the residue ($-R_3'$) of a compound of the formula (14) as mentioned below, with a compound of the formula:

$R_3'-H$     (14)

wherein $R_3'$ is as defined above, or its reactive derivative at the mercapto group.

Suitable reactive derivative at the mercapto group of the compound (14) include a metal salt such as an alkali metal salt (e.g. sodium or potassium salt), an alkaline earth metal (e.g. magnesium salt) and the like.

The reaction of the process 3 is usually carried out in a solvent such as water, acetone, chloroform, nitrobenzene, dimethylformamide, methanol, ethanol, dimethylsulfoxide, or any other organic solvents which do not adversely influence to the reaction, preferably in a rather highly polar solvent. The hydrophilic solvents may be used in a mixture with water. The reaction is preferably carried out in around neutral medium. When the compound (1-2) or (14) is used in a free form, the reaction is preferably conducted in the presence of a base such as alkali metal hydroxide, alkali metal carbonate, alkali metal bicarbonate, trialkylamine, or the like. The reaction temperature is not critical, and the reaction is usually carried out at room temperature or slightly elevated temperature.

The starting compound (1-2) can be prepared by the processes 1 and 2.

Process 4

Among the object compound (1), some compounds of the formula:

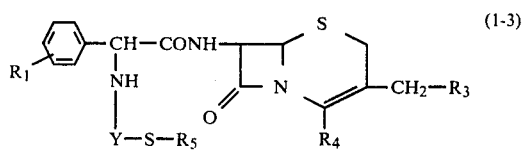
(1-3)

where $R_1$, $R_3$, $R_4$ and $R_5$ are each as defined above, and Y is an alkanoyl group or a salt thereof, can be prepared by process 4 which comprises reacting a compound of the formula:

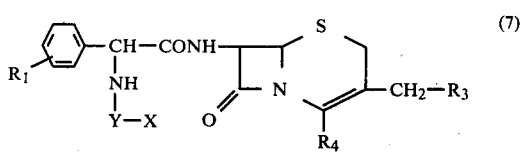
(7)

wherein $R_1$, $R_3$, $R_4$, $R_5$ and Y are each as defined above and X is a group capable of being replaced by the group $R_5$-S- of the compound (8) as mentioned below, or its salt, with a compound of the formula:

$R_5$-SH     (8)

wherein $R_5$ is as defined above, or its salt,

The group capable of being replaced by the group represented by X includes all conventional one like an acid residue such as halogen, azido, an acyloxy group which has the acyl moiety as mentioned above and are preferably lower alkanoyloxy (e.g. formyloxy, acetoxy, propionyloxy, butyryloxy or isobutyryloxy) or aroyloxy (e.g. benzyloxy or toluoyloxy) or the like, and organic sulfonyloxy such as mesyloxy, benzenesulfonyloxy or p-tosyloxy.

As the salt of the thiol compound (8), is preferably employed a salt with an alkali metal such as sodium or potassium.

The reaction of the process 4 is usually carried out in a conventional solvent such as water, acetone, chloroform, nitrobenzene, dimethylformamide, methanol, ethanol, dimethylsulfoxide, or any other rather high polar solvents which do not adversely influence to the reaction, and a mixture thereof. The reaction is preferably carried out in around neutral condition. When the compound (7) and/or the compound (8) are used in a free form, the reaction is preferably conducted in the presence of an organic or inorganic base such as alkali metal hydroxide, alkali metal carbonate, alkali metal bicarbonate, trialkylamine, pyridine or the like. The reaction temperature is not critical, and the reaction is usually carried out at room temperature or slightly elevated temperature.

The starting compound (7) can be prepared, for example, by reacting the compound (2) with a compound of the formula:

X—Y—X'     (15)

wherein X and Y are each as defined above and X' is halogen.

Process 5

Some object compound (1) of the formula:

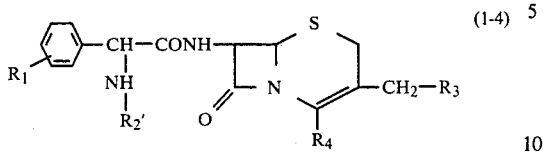

wherein $R_1$, $R_3$ and $R_4$ are each as defined above, and $R_2'$ is a 5-membered heterocyclic group containing two or three hetero atoms selected from N,O and S, a 5-membered heterocyclic group containing four hetero atoms selected from N,O and S or a 6-membered heterocyclic group containing two or three hetero atoms selected form N,O and S, in which those heterocyclic groups are each substituted with amino, can be prepared by hydrolysing a compound of the formula:

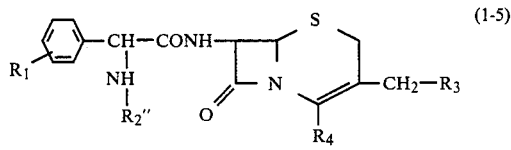

wherein $R_1$, $R_3$ and $R_4$ are each as defined above, and $R_2''$ is an alkanoyl substituted with said heterocyclic group defined for $R_2'$ in the compound (1-4), provided that it is substituted with N', N'-dialkylaminoalkylideneamino, in place of the amino group, or its salt.

The hydrolysis of this process is conducted by a conventional manner, and preferably in an acidic condition.

Suitable examples of the acid used for realizing the acidic hydrolysis condition are an inorganic acid such as hydrochloric acid, hydrobromic acid or sulfuric acid and an organic acid such as formic acid, acetic acid, chloroacetic acid, trifluoroacetic acid or p-toluenesulfonic acid.

The reaction of this process is usually carried out in a conventional solvent such as water, methanol, ethanol, acetone, chloroform, nitrobenzene, dimethylformamide, dimethylsulfoxide, or any other rather high polar solvents which do not adversely influence to the reaction, and a mixture thereof.

The reaction temperature is not critical, and the reaction is usually carried out from under cooling to slightly elevated temperature.

The starting compound (1-5) can be prepared by the process (1).

In accordance with the processes of this invention, the product can be separated and isolated from the reaction mixture and purified by the methods commonly used in the art, for example, extraction, precipitation, chromatography, crystallization or recrystallization.

In case that the object compound (1) having free amino and/or free carboxy group is obtained, it can be optionally transformed into its corresponding salt by a conventional method.

In case that the substituent(s) born on the object compounds (1), (1-1) and (1-3) and the starting compounds (3), (5), (1-2) and (8) was selected from hydroxy, oxo, amino, imino, mercapto and thioxo, there may occasionally exist a pair of every two tautomeric isomers thereof due to the tautomerism illustrated below:

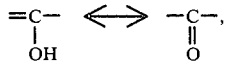

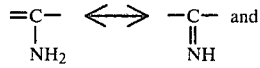

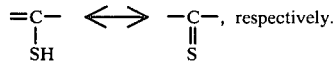

Therefore, these types of the isomers of all the compounds disclosed in this specification are of course to be included in the scope of this invention.

The compound (1) and a salt thereof provided by this invention are possessed of antibacterial activity and inhibit the growth of a number of pathogenic microorganisms including Gram-positive and Gram-negative bacteria. In practical administration for a therapeutical purpose, the free form or the pharmaceutically acceptable salts of the compound (1) is preferably used.

For therapeutic administration, the cephalosporin compounds according to this invention are used either orally or parenterally in a form of pharmaceutical preparation which contain said compounds in admixture with a pharmaceutically acceptable carriers such as an organic or inorganic solid or liquid excipient suitable for oral or parenteral administration. The pharmaceutical preparations may be, for example, in solid form such as capsules, tablets, trouches, ointments or suppositories, or in liquid form such as solutions, suspensions, or emulsions. If desired, there may be included in the above preparations auxiliary substances, stabilizing agents, wetting or emulsifying agents, buffers and other commonly used additives.

While the dosage of the compound (1) will vary depend upon the age and conditions of the patient, an average single dose of about 50 mg., 100 mg., 250 mg., 500 mg., 1 g. and 2 g. of the compounds according to the present invention has proved to be effective in treating infectious diseases caused by bacteria. In general, amounts between 1 g. and about 20 g. or even more amounts of the compound (1) may be administered daily.

For the purpose of illustrating of usefulness of the object compound (1) of this invention, the following minimal inhibitory concentrations of some representative compounds against some test strains will be shown.

Test Method

The minimal inhibitory concentration (MIC) was determined by the two-fold agar-plate dilution method as described below.

One loopful of an overnight culture of each test strain in Trypticase-soy broth was streaked on heart infusion agar (HI-agar) containing graded concentrations of representative antibiotic, and the MICs were expressed in terms of $\mu g/ml$. after incubation at 37° C. for 20 hours.

Test compounds and results (MIC)

| Test Bacteria ($10^8$ viable cells per ml) | Test Compound [mcg/ml] | |
|---|---|---|
| | Compound of Example (1-10) | Compound of Example (1-31) |
| Staph. Aureus 209-P | 0.78 | 1.56 |
| B. Subtilis ATCC-6633 | 0.20 | 0.78 |
| Sal. Enteritidis | 0.78 | 0.39 |

| Test Compound (mcg.ml) | Test Bacteria | | |
|---|---|---|---|
| | Sh. flexneri 2a* | Sal. Enteritides* | Ps. Aeruginosa** |
| Compound of Example 1-31 | 0.2 | See the above table. | 0.78 |
| Compound of Example 1-34 | 0.2 | 0.2 | 0.78 |
| Compound of Example 1-35 | 0.39 | 0.78 | |
| Compound of Example 1-36 | 0.39 | 0.78 | 1.56 |
| Compound of Example 1-37 | 0.1 | 0.05 | 0.78 |

*$10^8$ viable cells per ml
**$10^6$ veable cells per ml

| Test Compound | Ps. Aeruginosa 721 ($10^6$ viable cells per ml) [mcg/ml] |
|---|---|
| (1-1) | 0.39 |
| (1-6) | 1.56 |
| (1-10) | 0.39 |
| (1-16) | 1.56 |
| (1-20) | 0.78 |
| (2-1) | 0.39 |

| Test Compound (mcg.ml) | Test Bacteria | | |
|---|---|---|---|
| | Sh. flexneri 2a* | Sal. Enteritides* | Ps. Aeruginosa** |
| Compound of Example 1-31 | 0.2 | See the above table. | 0.78 |
| Compound of Example 1-34 | 0.2 | 0.2 | 0.78 |
| Compound of Example 1-35 | 0.39 | 0.39 | 0.78 |
| Compound of Example 1-36 | 0.39 | 0.78 | 1.56 |
| Compound of Example 1-37 | 0.1 | 0.05 | 0.78 |

*$10^8$ viable cells per ml
**$10^6$ veable cells per ml

| Test Compound | Ps. Aeruginosa 721 ($10^6$ viable cells per ml) [mcg/ml] |
|---|---|
| (1-1) | 0.39 |
| (1-6) | 1.56 |
| (1-10) | 0.39 |
| (1-16) | 1.56 |
| (1-20) | 0.78 |
| (2-1) | 0.39 |

The following preparations and examples are given for the purpose of illustrating the present invention.

Preparation 1

[Preparation of compound (3)]

(1) A mixture of 2-hydroxymethyl-5-hydroxy-4H-pyran-4-one (1.42 g), ethyl 2-bromoacetate (2.0 g), potassium carbonate (1.38 g) and potassium iodide (50 mg) in dry acetone was refluxed for 6 hours. An insoluble substance was filtered off, and the acetone was evaporated. The residue was extracted with ethyl acetate (50 ml), and the extract was washed with water (20 ml), 10% hydrochloric acid, and an aqueous solution of sodium chloride in turn, dried and concentrated.

The residual pale yellow oil (3.0 g) was washed with n-hexane (20 ml) twice with shaking and crystallized by addition of a mixture of benzene and n-hexane. The resulting crystals were collected by filtration and dried to give crystals (2.15 g). Thus obtained crystals (1 g) were recrystallized from benzene (30 ml) to give crystals (0.9 g) of ethyl 2-(4-oxo-6-hydroxymethyl-4H-pyran-3-yloxy)acetate monohydrate, mp 52° to 53° C.

(2) A mixture of ethyl 2-(4-oxo-6-hydroxymethyl-4H-pyran-3-yloxy)acetate monohydrate (10 g) in conc. ammonia was heated at 120° C. for 10 hours in a sealed vessel and the reaction mixture was concentrated. To the residue was added water and the resultant solution was adjusted to pH 1 to 2 with 10% hydrochloric acid. The resultant precipitates were washed with water and dried to give crystals (6 g) of 2-(4-oxo-6-hydroxymethyl-1,4-dihydropyridin-3-yloxy)acetic acid.

U.V. Spectrum $\lambda_{max}^{0.1\,N\,HCl}$ 244,278 nm.

(3) 2-(4-Oxo-6-hydroxymethyl-1,4-dihydropyridin-3-yloxy)acetic acid (5.97 g) was dissolved in a mixture of methanol (300 ml) and water (420 ml) at 65° to 70° C. and the solution was stirred at the same temperature. Trichloroisocyanuric acid (2.79 g) was added thereto, and the resultant mixture was stirred at the same temperature for 1.5 hours and then allowed to stand at room temperature over-night. The reaction mixture was cooled and the resulting crystals were collected by filtration, washed with water and dried. Thus obtained crystals (4.1 g) were recrystallized from water (100 ml) to give crystals (3.4 g) of 2-(4-oxo-5-chloro-6-hydroxymethyl-1,4-dihydropyridin-3-yloxy) acetic acid, mp 240° to 245° C.(dec).

(4) To crystals (10 g) of 2-(4-oxo-6-hydroxymethyl-1,4-dihydropyridin-3-yloxy)acetic acid was added thionyl chloride (25 ml), and the mixture was stirred for 30 minutes. After cooling, dimethylformamide (125 ml) was added to the reaction mixture, and the resultant mixture was stirred for an hour. The resultant mixture was poured into cold water (750 ml) and the aqueous solution was adjusted to pH 3 with an aqueous sodium bicarbonate solution and then cooled with ice for 2 hours. Precipitated crystals were collected by filtration and washed with water to give crystals (8.7 g) of 2-(4-oxo-6-chloromethyl-1,4-dihydropyridin-3-yloxy)acetic acid. (This product was converted to its hydrochloride monohydrate, m.p. 150° to 155° C. by recrystallizing from a mixture of 10% hydrochloric acid (5 ml) and water (5 ml).

(5)-(1) A mixture of ethyl 2-(4-oxo-6-hydroxymethyl-4H-pyran-3-yloxy)acetate monohydrate (26.4 g) and thionyl chloride (60 ml) was allowed to stand at room temperature for an hour. After removal of the excess of thionyl chloride, ethyl acetate was added to the residue and the solution was washed with an aqueous solution saturated with sodium chloride. The ethyl acetate layer was dried over magnesium sulfate and concentrated. The residue was triturated with a mixture of benzene and petroleum ether to give crystals (16.5 g). Recrystallization from carbon tetrachloride gave crystals of ethyl 2-(4-oxo-6-chloromethyl-4H-pyran-3-yloxy)acetate, mp 98° to 100° C.

(5)-(2) To a solution of 2-chloromethyl-5-hydroxy-4H-pyran-4-one (3.2 g), ethyl 2-bromoacetate (3.4 g) in dry dimethylformamide (100 ml) was bit by bit added 50% sodium hydride (960 mg) at room temperature under stirring, and the mixture was stirred at room temperature for an hour. The reaction mixture was poured into ice-water, and an insoluble substance was filtered off. The filtrate was adjusted to pH 3 with 10% hydrochloric acid and extracted with diethyl ether. The extract was dried and concentrated. The crystalline residue was triturated with a mixture of petroleum ether and benzene and collected by filtration and dried to give crystals (2.5 g), which were recrystallized from carbon tetrachloride to give crystals of ethyl 2-(4-oxo-6-chloromethyl-4H-pyran-3-yloxy)acetate, mp 98° to 100° C.

(6) A mixture of ethyl 2-(4-oxo-6-chloromethyl-4H-pyran-3-yloxy)acetate (16.0 g) in acetic acid (80 ml) was stirred at room temperature, and zinc (8.0 g) was added thereto. The resultant mixture was stirred at room temperature for 4 hours and filtered. The filtrate was concentrated and ethyl acetate was added thereto. The mixture was adjusted to pH 8 with 5% sodium bicarbonate aqueous solution and an insoluble substance was filtered off. The ethyl acetate layer was dried over magnesium sulfate and concentrated. Benzene was added to the residue, the resulting crystals were collected by filtration, and dried to give crystals (8.3 g), which were recrystallized from benzene to give crystals of ethyl 2-(4-oxo-6-methyl-4H-pyran-3-yloxy)acetate, mp 95° to 98° C.

(7) A mixture of ethyl 2-(4-oxo-6-methyl-4H-pyran-3-yloxy)acetate (6.36 g) and conc. ammonia (30 ml) was heated at 120° C. for 10 hours. The reaction mixture was concentrated, and water (50 ml) was added to the residue. The resultant aqueous mixture was adjusted to pH 2 to 3 with 10% hydrochloric acid. The resulting precipitates were collected by filtration and washed with water to give crystals (4.5 g) of 2-(4-oxo-6-methyl-1,4-dihydropyridin-3-yloxy)acetic acid dihydrate, mp 235° to 236° C. (dec.).

(8) 2-(4-oxo-6-methyl-1,4-dihydropyridin-3-yloxy)acetic acid dihydrate (2.2 g) was dissolved in a mixture of methanol (120 ml) and water (170 ml) under heating on a water bath. The solution was stirred at 65° to 70° C. and trichloroisocyanuric acid (1.1 g) was added thereto. The resultant mixture was stirred for 65° to 70° C. for 1.5 hours. The reaction mixture was left to cool to room temperature with removal of the water bath and filtered. The obtained precipitates were washed with water and dried. The resultant crystals (2.0 g) were dried at 100° C. for 6 hours in vacuo over phosphorus pentoxide to give crystals of 2-(4-oxo-5-chloro-6-methyl-1,4-dihydropyridin-3-yloxy)acetic acid dihydrate, mp 240° to 242° C.

(9) A mixture of ethyl 2-(4-oxo-6-methyl-4H-pyran-3-yloxy)acetate (8.3 g) in 1 N sodium hydroxide (40 ml) was stirred at room temperature for 30 minutes. To the mixture was added further 1 N sodium hydroxide (6 ml) and the resultant mixture was stirred for 30 minutes. To the reaction mixture was added dropwise conc. hydrochloric acid (4 ml) under ice-cooling, and resulting crystals were collected by filtration, washed with water, and dried to give crystals (6.8 g) of 2-(4-oxo-6-methyl-4H-pyran-3-yloxy)acetic acid.

I.R. Spectrum (Nujol) 1700, 1670, 1620 cm$^{-1}$.

(10) To a stirred solution of 40% aqueous methylamine (9.0 ml) and water (9.0 ml) was added 2-(4-oxo-6-methyl-4H-pyran-3-yloxy)acetic acid (6.0 g) in small portions at room temperature. The mixture was stirred at the same temperature for 3 hours and concentrated. To the residue was added water (5 ml) and the mixture was adjusted to pH 3. The resulting precipitates were collected and washed with water to give crystals of 2-(1,6-dimethyl-4-oxo-1,4-dihydropyridin-3-yloxy)acetic acid (1.53 g), mp 240° to 242° C. The filtrate and the washings were combined together and adsorbed on Amberlite IRA-400 (Tradename, prepared by Rohm and Haas Co.) and eluted with water and then 0.3 N hydrochloric acid. The hydrochloric acid fraction was concentrated and dried to give crystals (3.7 g) of 2-(1,6-dimethyl-4-oxo-1,4-dihydropyridin-3-yloxy)acetic acid hydrochloride. The hydrochloride was dissolved in a small amount of water and the solution was adjusted to pH 3. The resulting crystals were collected by filtration and washed with water to give an additional amount of the same product (2.2 g) as obtained above.

(11) Sodium (7.13 g) in toluene (80 ml) was stirred below 30° C., and a mixture of dimethyl 2,2'-oxydiacetate (50 g) and ethyl formate (23 g) in toluene (20 ml) was dropwise added thereto. The resultant mixture was stirred for 4 hours below 30° C. and allowed to stant over-night. To the reaction mixture was added ethanol (80 ml) and the mixture was stirred for 15 minutes, after which thiourea (22.8 g) added thereto. The mixture was stirred for an hour and refluxed for 5 hours. After removal of the solvent, ethyl acetate and 10% hydrochloric acid was added to the residue, whereby the resultant mixture was adjusted to pH 3. An insoluble substance was filtered off and the ethyl acetate layer was washed with water, dried over magnesium sulfate and concentrated. The residue (50 g) was subjected to column chromatography on silica gel with an eluent (ethyl acetate (1)+benzene (1)) to give crystals (6.5 g). Thus obtained crystals were recrystallized from ethyl acetate to give crystals (4.5 g) of ethyl 2-(2-mercapto-4-hydroxy-5-pyrimidyloxy)acetate, mp 157° to 160° C. Thus obtained crystals (4.0 g) and sodium bicarbonate (1.6 g) were dissoved in water (50 ml) under heating and the resultant solution was stirred. Raney nickel (12 g) was bit by bit added thereto and the mixture was stirred at room temperature for 2 hours. The reaction mixture was filtered and the filtrate was adjusted to pH 2 with conc. hydrochloric acid under ice-cooling. The resulting precipitates were collected by filtration, washed with water and dried to give crystals (1.0 g) of 2-(4-oxo- 1,4-dihydropyrimidin-5-yloxy)acetic acid, mp 180° to 185° C. (dec.).

(12) 1-Hydroxy-1,2-dihydropyrazin-2-one (9 g) was dissolved in dimethylformamide (80 ml) under heating and the solution was stirred under cooling. 65% Sodium hydride (3 g) was bit by bit added thereto and, 30 minutes after, ethyl 2-bromoacetate (13.4 g) was added thereto. The mixture was stirred for 2 hours at 60° to 70° C., and the reaction mixture was cooled and poured onto ice. The resultant aqueous solution was extracted with ethyl acetate, and the extract was dried over magnesium sulfate and concentrated. The crystalline residue was recrystallized from a mixture of benzene and petroleum ether to give crystals (6.5 g), which were further recrystallized from benzene to give crystals (6.0 g) of ethyl 2-(2-oxo-1,2-dihydropyrazin-1-yloxy)acetate, mp 98° to 100° C. Thus obtained crystals (2.97 g) were added to 1 N potassium hydroxide (15 ml) and the mixture was stirred for an hour under ice-cooling. The resulting solution was lyophilized to give powder (3.1 g) of potassium 2-(2-oxo-1,2-dihydropyrazin-1-yloxy)acetate.

N.M.R. Spectrum ($D_2O$, δ) Internal standard: 3-(trimethylsilyl)propionic acid Na salt-$D_4$ ppm 4.68 (2H, s), 7.50 (1H, d, J=5 Hz), 8.08 (1H, d, J=5 Hz), 8.25 (1H, s).

(13) A mixture of ethyl 2-(4-oxo-6-methyl-4H-pyran-3-yloxy)acetate (8.2 g) and phosphorus pentasulfide (4.4 g) in dry benzene (800 ml) was stirred for 2.5 hours at 60° C. After removal of an isoluble substance by decantaion from the hot reaction mixture, the reaction solution was concentrated. To the residue were added ethyl acetate, water and an aqueous solution of sodium bicarbonate, whereby the resultant mixture was adjusted to pH 8, and ethyl acetate layer was washed with an aqueous solution saturated with sodium chloride and dried over magnesium sulfate. Removal of the solvent gave a crystalline residue (7.0 g), which was recrystallized from carbon tetrachloride (25 ml) and washed with petroleum ether to give crystals (6.5 g) of ethyl 2-(4-thioxo-6-methyl-4H-pyran-3-yloxy)acetate.

N.M.R. Spectrum (Acetone-$D_6$, δ) Internal standard: Trimethylsilan ppm 1.25 (3H, t, J=7 Hz), 2.28 (3H, s), 4.22 (2H, q, J=7 Hz), 4.75 (2H, s), 7.18 (1H, s), 8.02 (1H, s).

Thus obtained crystals (2.8 g) in 10% hydrochloric acid (50 ml) and ethanol (25 ml) were stirred at 80° C. for 2 hours. To this mixture was added further 10% hydrochloric acid (20 ml) and the resultant mixture was stirred at 100° C. for 2 hours. After removal of the ethanol, the residue was cooled and resulting precipitates were collected by filtration, washed with water and benzene and dried. Thus obtained crystals (1.8 g) were dissolved in ethyl acetate (100 ml), dried over magnesium sulfate and treated with active charcoal. Removal of the ethyl acetate gave yellowish crystals (1.7 g) of 2-(4-thioxo-6-methyl-4H-pyran-3-yloxy)acetic acid, mp 120° to 125° C.

(14) To a solution of 2-(4-oxo-1,4-dihydropyridin-3-yloxy)acetic acid (16.9 g) in 0.5 N sodium hydroxide aqueous solution (200 ml), was added dropwise under cooling a sodium hypochlorite aqueous solution (70 ml) whose active chlorine is about 10% at 3° to 8° C. with stirring. The mixture was stirred for 30 minutes at the same temperature and adjusted to pH 3 with 10% hydrochloric acid. Precipitated crystals were collected by filtration, recrystallized from 1 N hydrochloric acid and dried at 90° to 95° C. for 4-5 hours in a stream of air to give crystals (16.7 g) of 2-(4-oxo-5-chloro-1,4-dihydropyridin-3-yloxy)acetic acid, mp 253° to 255° C.

(15)-(1) A mixture of 3-hydroxy-4H-pyran-4-one (1.12 g), ethyl 2-bromoacetate (1.7 g) and potassium carbonate (1.4 g) in ethanol (30 ml) was stirred at 67° to 70° C. for 75 minutes. The reaction mixture was allowed to stand at room temperature. An insoluble substance was filtered off, and the filtrate was adjusted to pH 4 to 5 with conc. hydrochloric acid and the ethanol was removed. To the residue was added ethyl acetate, and the resultant mixture was washed with an aqueous solution saturated with sodium chloride and dried over magnesium sulfate. After removal of the solvent, the residue was chromatographed on silica gel (15 g) with an eluent (ethyl acetate:benzene=1:5) to give crystals of ethyl 2-(4-oxo-4H-pyran-3-yloxy)acetate, mp 58° to 60° C.

(15)-(2) A mixture of ethyl 2-(4-oxo-4H-pyran-3-yloxy)acetate (198 g) in 10% hydrochloric acid (10 ml) was heated at 70° to 75° C. for an hour under stirring. The reaction mixture was cooled and concentrated to the volume of about 5 ml. Precipitated crystals were collected by filtration washed with water and dried to give crystals (1.8 g) of 2-(4-oxo-4H-pyran-3-yloxy)acetic acid monohydrate, mp 155° to 157° C.

(15)-(3) A mixture of 2-(4-oxo-4H-pyran-3-yloxy)acetic acid monohydrate (6.5 g) and conc. aqueous ammonia (65 ml) was stirred for 4.5 hours at room temperature, and the aqueous ammonia was evaporated. To the residue was added water (60 ml) and the resultant solution was adjusted to pH 6 with 10% hydrochloric acid. Active charcoal (2 g) was added thereto and filtrated during the mixture was hot. The filtrate was adjusted to pH 3 with 10% hydrochloric acid and allowed to stand in a refrigerator. The appearing crystals were collected by filtration and washed with cold water to give yellow crystals (1.5 g), mp 267° and 268° C. (dec). These crystals were dried at 90° C. for 6 hours in vacuo over phosphorus pentoxide to give crystals (1.45 g) of 2-(4-oxo-1,4-dihydropyridin-3-yloxy)acetic acid, mp 260° to 262.5° C. (dec).

Preparation 2

[Preparation of compound (5)]

A mixture of 2-(4-oxo-5-chloro-6-methyl-1,4-dihydropyridin-3-yloxy)acetic acid dihydrate (4.32 g) and triethylamine (4 ml) in methylene chloride (50 ml) was stirred at room temperature, and the resultant solution was concentrated under vacuum. To the residue was dropwise added a solution of thionyl chloride (2.38 g) in methylene chloride (30 ml) at 15° to 20° C. and the resultant mixture was stirred for 10 minutes. The resulting precipitates were collected by filtration and added to a suspension of D-2-(4-hydroxyphenyl)glycine (2.86 g) and bis(trimethylsilyl)acetamide (9 ml) in methylene chloride (90 ml). The resultant mixture was stirred at room temperature for 2 hours, allowed to stand overnight and concentrated under vacuum. The residual oil was solidified by addition of water (100 ml) followed by stirring for 2 hours. The resulting crystals were collected by filtration, washed with water and dried to give crystals (5.35 g) of D-2-[2-(4-oxo-5-chloro-6-methyl-1,4-dihydropyridin-3-yloxy)acetamido]-2-(4-hydroxyphenyl)acetic acid, mp 197° to 198° C. (dec.). Recrystallization from hot water gave crystals having mp 202° to 203° C. (dec), which was analysed by Karl-Fisher's method to reveal ½ molar equivalent water.

Example 1

(1) A mixture of 4-hydroxy-3-furazancarboxylic acid (650 mg) in thionyl chloride (20 ml) was heated under reflux for an hour and excess thionyl chloride was distilled off under reduced pressure. The residue containing 4-hydroxy-3-furazancarbonyl chloride was dissolved in acetone (10 ml) and the solution was dropwise added at 0°–5° C. to a solution of 7-(D-2-phenylglycinamido)-3-(1-methyl-1H-tetrazol-5-ylthiomethyl)-3-cephem-4-carboxylic acid (2.5 g) and bis(trimethylsilyl)acetamide (5 ml) in methylene chloride (50 ml). The resultant mixture was stirred at 0°–5° C. for an hour. After removal of the solvent, ethyl acetate and water were added to the residue, and the mixture was adjusted to pH 1 with 10% hydrochloric acid under stirring, after which the organic layer was separated and extracted with an aqueous solution of sodium bicarbonate. Ethyl acetate was added to the aqueous extract and the mixture was adjusted to pH 1 with 10% hydrochloric acid. The ethyl acetate layer was separated, washed with water and dried over magnesium sulfate. The solvent was distilled off under reduced pressure. The resultant powder (2.5 g) was dissolved in acetone and treated with active charcoal (2.5 g), after which the solvent was distilled off and the resultant powder was washed with diethyl ether to give powder (2.1 g) of 7-[D-2-(4-hydroxy-3-furazancarboxamido)-2-phenylacetamido]-3-(1-methyl-1H-tetrazol-5-ylthiomethyl)-3-cephem-4-carboxylic acid, mp 133° to 135° C. (dec).

(2) A mixture of 3-(2-chlorophenyl)-5-methyl-4-isoxazolecarboxylic acid (1.4 g) and thionyl chloride (1.4 ml) was heated under reflux for 2 hours and, after removal of thionyl chloride, the residue containing 3-(2-chlorophenyl)-5-methyl-4-isoxazolecarbonyl chloride was dissolved in methylene chloride. The resultant solution wad dropwise added at 0°–5° C. to a solution of 7-(D-2-phenylglycinamido)-3-(1-methyl-1H-tetrazol-5-ylthiomethyl)-3-cephem-4-carboxylic acid (2.3 g) and bis(trimethylsilyl)acetamide (4.0 g) in methylene chloride (50 ml), and the resultant mixture was stirred at 5° C. for an hour. The solvent was distilled off under reduced pressure and to the residue was added water and ethyl acetate. The resultant mixture was adjusted to pH 2 with 10% hydrochloric acid under stirring. The ethyl acetate layer was separated and extracted with an aqueous solution of sodium bicarbonate. An appearing insoluble substance was collected by filtration and suspended in water. To the resultant suspension was added ethyl acetate, and the mixture was adjusted to pH 2 with 10% hydrochloric acid under stirring. The organic layer was washed with water and dried over magnesium sulfate, after which the solvent was removed. The remaining powder (2.2 g) was dissolved in acetone and treated with active charcoal (2.2 g). After removal of acetone, the residue was washed with diisopropyl ether to give powder (1.6 g) of 7-{D-2-[3-(2-chlorophenyl)-5-methyl-4-isoxazolecarboxamido]-2-phenylacetamido}-3-(1-methyl-1H-tetrazol-5-ylthiomethyl)-3-cephem-4-carboxylic acid, mp 101° to 103° C. (dec).

(3) Powder (1.9 g) of 7-[D-2-(2-thenoylamino)-2-phenylacetamido]-3-(1-methyl-1H-tetrazol-5-ylthiomethyl)-3-cephem-4-carboxylic acid, mp 98° to 101° C. (dec) was obtained in a similar manner to that of Example (1-1), reacting an oil containing 2-thenoyl chloride, which was prepared from 2-thenoic acid (640 mg) and thionyl chloride (7 ml), with a solution of 7-(D-2-phenylglycinamido)-3-(1-methyl-1H-tetrazol-5-ylthiomethyl)-3-cephem-4-carboxylic acid (2.3 g) and bis(trimethylsilyl) acetamide (4.0 g) in methylene chloride (50 ml).

(4) To a mixture of 3-methylthio-5-hydroxy-1,2,4-triazine-6-carboxylic acid (935 mg) and triethylamine (500 mg) in methylene chloride (40 ml), was dropwise added at 0° to 5° C. a solution of thionyl chloride (600 mg) in methylene chloride (2 ml), and the resultant mixture was stirred for 75 minutes at the same temperature. To the reaction mixture containing 3-methylthio-5-hydroxy-1,2,4-triazine-6-carbonyl chloride was added a solution of 7-(D-2-phenylglycinamido)-3-(1-methyl-1H-tetrazol-5-ylthiomethyl)-3-cephem-4-carboxylic acid (2.50 g) and bis(trimethylsilyl)acetamide (4.0 g) in methylene chloride (50 ml). The resultant mixture was stirred at 0°–5° C. for an hour and further at room temperature for 30 minutes. After removal of the solvent, an aqueous solution of sodium bicarbonate (80 ml) was added to the residue and the mixture was washed three times with ethyl acetate. The aqueous solution was layered with ethyl acetate (40 ml), and adjusted to pH 1 with 10% hydrochloric acid under stirring. An appearing insoluble substance was collected by filtration to give powder (1.41 g). The organic layer of the filtrate was separated, dried over magnesium sulfate and condensed to about 10 ml of its volume. An appearing insoluble substance was collected by filtration to give powder (0.22 g). Thus obtained powder (0.22 g) and the above obtained powder (1.41 g) were combined together and dissolved in a 3.3% sodium bicarbonate aqueous solution (30 ml). The aqueous solution was stirred with active charcoal at room temperature for 15 minutes. The charcoal was filtered and washed with water. The filtrate and the washings were combined together, layered with ethyl acetate and adjusted to pH 2 with 10% hydrochloric acid under stirring. An appearing insoluble substance was collected by filtration, washed with ethyl acetate, water and ethyl acetate in turn and dried to give powder (1.15 g) of 7[D-2-(3-methylthio-5-hydroxy-1,2,4-triazine-6-carboxamido)-2-phenylacetamido]-3-(1-methyl-1H-tetrazol-5-ylthiomethyl)-3-cephem-4-carboxylic acid, mp 178°–183° C. (dec).

(5) In a similar manner to that of Example (1-4), 3-mercapto-5-hydroxy-1,2,4-triazine-6-carbonyl chloride, which was prepared from 3-mercapto-5-hydroxy-1,2,4-triazine-6-carboxylic acid (1.73 g), triethylamine (1.0 g), dimethylformamide (30 ml) and thionyl chloride (1.19 g), was treated with a mixture of 7-(D-2-phenylglycinamido)-3-(1-methyl-1H-tetrazol-5-ylthiomethyl)-3-cephem-4-carboxylic acid (4.0 g) and bis(trimethylsilyl) acetamide (6.4 g) in methylene chloride (40 ml). Thus obtained reaction mixture was worked up in a similar manner to that of Example (1-1) to give power (870 mg) of 7-[D-2-(3-mercapto-5-hydroxy-1,2,4-triazine-6-carboxamido)-2-phenylacetamido]-3-(1-methyl-1H-tetrazol-5-ylthiomethyl)-3-cephem-4-carboxylic acid, mp 175° to 179° C. (dec).

(6) In a similar manner to that of Example (1-1), 4-oxo-4H-pyrido[1,2-a]pyrimidine-3-carbonyl chloride, which was prepared from 4-oxo-4H-pyrido[1,2-a]pyrimidine-3-carboxylic acid (1.8 g) and thionyl chloride (36 ml), was treated with a solution of 7-(D-2-phenylglycinamido)-3-(1-methyl-1H-tetrazol-5-ylthiomethyl)-3-cephem-4-carboxylic acid formate (2.5 g) and bis(trimethylsilyl)acetamide (4.0 g) in methylene chloride (50 ml). Thus obtained reaction mixture was worked up in a similar manner to that of Example (1-4) to give powder (650 mg) of 7-[D-2-(4-oxo-4H-pyrido[1,2-a]pyrimidine-3-carboxamido)-2-phenylacetamide]-3-(1-methyl-1H-tetrazol-5-ylthiomethyl)-3-cephem-4-carboxylic acid, mp 103° to 105° C. (dec).

(7) To a mixture of 2-(5-methyl-1,3,4-thiadiazol-2-yloxy)acetic acid (1.74 g) and triethylamine (1.01 g) in methylene chloride (50 ml) was dropwise added at −5° to 0° C. with stirring a solution of thionyl chloride (1.2 g) in methylene cgloride (10 ml). The resultant mixture was stirred at −5° to 0° C. for an hour, and ⅞ parts of the reaction mixture containing 2-(5-methyl-1,3,4-thiadiazol-2-yloxy)acetyl chloride was added to a solution of 7-(D-2-phenylglycinamido)-3-(1-methyl-1H-tetrazol-5-ylthiomethyl)-3-cephem-4-carboxylic acid (2.5 g) and bis(trimethylsilyl)acetamide (6 ml) in methylene chloride (150 ml). The resultant mixture was stirred at −5° to 0° C. for 30 minutes and at room temperature for further 30 minutes, and treated in a similar manner to that of Example (1-1) to give powder (1.7 g). Thus obtained powder was suspended in a mixture of acetone (5 ml) and ethyl acetate (5 ml), stirred and filtered. The resultant powder was washed with ethyl acetate and then diethyl ether to give powder (1.2 g) of 7-{D-2-[2-(5-methyl-1,3,4-thiadiazol-2-yloxy)acetamido]-2-phenylacetamido}-3-(1-methyl-1H-tetrazol-5-ylthiomethyl)-3-cephem-4-carboxylic acid, mp 175° to 178° C. (dec).

(8) A mixture of dimethylformamide (365 mg) and thionyl chloride (1.2 g) was heated at 50° C. for 40 minutes and the excess of thionyl chloride was removed. To the residue was added methylene chloride (30 ml) and the resultant mixture was stirred at −25° to −20° C. To the reaction mixture was added 2-(4-oxo-6-chloromethyl-4H-pyran-3-yloxy)acetic acid (1.8 g) and then dimethylformamide (5 ml), and the resultant mixture was stirred at −25° to −20° C. for 30 minutes. To the reaction mixture containing 2-(4-oxo-6-chloromethyl-4H-pyran-3-yloxy) acetyl chloride was added at −25° to −20° C. under stirring a solution of 7-(D-2-phynylglycinamido)-3-(1-methyl-1H-tetrazol-5-ylthiomethyl)-3-cephem-4-carboxylic acid (2.5 g) and bis(trimethylsilyl)acetamide in methylene chloride (100 ml). The resultant mixture was stirred at −25° to −20° C. for 30 minutes and further kept under stirring until room temperature. After removal of the solvent, ethyl acetate and water was added to the residue under stirring and an insoluble substance was filtered off. The ethyl acetate layer was separated and extracted with a 5% sodium bicarbonate aqueous solution. To the aqueous extract was added ethyl acetate and the mixture was adjusted to pH 1-2 with 10% hydrochloric acid under stirring. The organic layer was separated, washed with water and than a saturated aqueous solution of sodium chloride, dried over magnesium sulfate and filtered through silica gel. After removal of the solvent, the residue was precipitated with a mixture of ethyl acetate and diethyl ether. The resultant powder (1.2 g) was dissolved in acetone and treated with active charcoal (2 g). The filtrate was condensed to a small volume and diluted with diethyl ether to give powder (0.8 g) of 7-{D-2-[2-(4-oxo-6-chloromethyl-4H-pyran-3-yloxy)acetamido]-2-phenylacetamido}3-(1-methyl-1H-tetrazol-5-ylthiomethyl)-3-cephem-4-carboxylic acid, mp 145° to 150° C. (dec).

(9) To a mixture of 5-phenyl-2-oxazolidinone (1.63 g), tetrahydrofuran (100 ml) and phosgene (0.015 mole) was dropwise added at 0°-5° C. a solution of triethylamine in tetrahydrofuran, and the resultant mixture was stirred at 0°-5° C. for an hour. The appearing triethylamine hydrochloride was filtered off and the solvent was distilled off under reduced pressure. The residue containing 2-oxo-5-phenyl-3-oxazolidinecarbonyl chloride was dissolved in benzene and an insoluble substance was filtered off. The benzene solution was concentrated and the oily residue was dissolved in methylene chloride. The resultant solution was dropwise added at 0°-5° C. to a solution of 7-(D-2-phenylglycinamido)-3-(1-methyl-1H-tetrazol-5-ylthiomethyl)-3-cephem-4-carboxylic acid (2.3 g) and bis(trimethylsilyl) acetamide in methylene chloride and the resultant mixture was stirred at 0°-5° C. for 2 hours and at room temperature for 30 minutes. The reaction mixture was treated in a similar manner to that of Example (1-1) to give powder (1.6 g), which was reprecipitated with a mixture of acetone and ethyl acetate to give powder (1.1 g) of 7-[D-2-(2-oxo-5-phenyl-3-oxazolidinecarboxamido)-2-phenylacetamido]-3-(1-methyl-1H-tetrazol-5-ylthiomethyl)-3-cephem-4-carboxylic acid, mp 115° to 120° C. (dec).

(10) In a similar manner to that of Example (1-9), 2-oxo-3-oxazolidinecarbonyl chloride, which was prepared from 2-oxazolidinone (1.04 g), phosgene (0.018 mole) and triethylamine (3.0 g) in tetrahydrofuran was treated with a solution of 7-(D-2-phenylglycinamido)-3-(1-methyl-1H-tetrazol-5-ylthiomethyl)-3-cephem-4-carboxylic acid (3.0 g) and bis(trimethylsilyl) acetamide (4.8 g) in methylene chloride (60 ml). The reaction mixture was worked up in a similar manner to that of Example (1-1) to give powder (1.92 g). This powder was dissolved into acetone and water was added thereto. The resultant mixture was concentrated, and a precipitated solid was collected by filtration to give powder (1.55 g) of 7-[D-2-(2-oxo-3-oxazolidinecarboxamido)-2-phenylacetamido]-3-(1-methyl-1H-tetrazol-5-ylthiomethyl)-3-cephem-4-carboxylic acid, mp 165° to 170° C. (dec).

(11) A mixture of 3-isoxazolidinone (700 mg) in tetrahydrofuran (30 ml) and phosgene (0.018 mole) was stirred at 0°-5° C. for 3.5 hours and the solvent was removed. Tetrahydrofuran was added to the residue and the solvent was again removed. The residue was dissolved in benzene and benzene was removed by decantation, and the residue was further evaporated and dissolved in methylene chloride (5 ml). The resultant solution containing 3-oxo-2-isoxazolidinecarbonyl chloride was dropwise added to a solution of 7-(D-2-phenylglycinamido)-3-(1-methyl-1H-tetrazol-5-ylthiomethyl)-3-cephem-4-carboxylic acid (2.0 g) and bis(trimethylsilyl)acetamide (3.2 g) in methylene chloride (50 ml) at 0°-5° C. and the resultant mixture was stirred at 0°-5° C. for 1.5 hour and at room temperature for an hour. After removal of the solvent, the residue was added to ethyl acetate (70 ml) and 5% hydrochloric acid (40 ml) and an insoluble substance was filtered off. The organic layer was washed with 5% hydrochloric acid and water and dried, and the solvent was distilled off under reduced pressure. The residue was pulverized with diethyl ether, the resultant crude powder (1.40 g) was treated with active charcoal in acetone and acetone was removed. The residue was pulverized with diethyl ether to give powder (0.94 g) of 7-[D-2-(3-oxo-2-isoxazolidinecarboxamido)-2-phenylacetamido]-3-(1-methyl-1H-tetrazol-5-ylthiomethyl)-3-cephem-4-carboxylic acid, mp 138° to 144° C. (dec).

(12) In a similar manner to that of Example (1-9), 2-oxo-3-thiazolidinecarbonyl chloride, which was prepared form 3-thiazolidinone (1.27 g), triethylamine (2.40 g) and phosgene (0.0273 mole) in tetrahydrofuran (60 ml), was treated with a solution of 7-(D-2-phenylglycinamido)-3-(1-methyl-1H-tetrazol-5-ylmethyl)-3-cephem-4-carboxylic acid (3.0 g) and bis (trimethylsilyl)acetamide (3.6 g) in methylene chloride (90 ml). The reaction mixture was worked up in a similar manner to that of Example (1-11) to give crude powder (3.90 g). The powder was added to ethyl acetate and extracted with a 5% sodium bicarbonate aqueous solution (100 ml) under ice-cooling. The aqueous extract was layered with ethyl acetate, adjusted to pH 4 with 10% hydrochloric acid under stirring and the aqueous layer was separated. The aqueous layer was further extracted with ethyl acetate, and both ethyl acetate layers obtained here and in the above were combined, washed with water and dried. After removal of the solvent, the residue was pulverized with diethyl ether to give powder (2.02 g) of 7-[D-2-(2-oxo-3-thiazolidinecarboxamido)-2-phenylacetamido]-3-(1-methyl-1H-tetrazol-5-ylthiomethyl)-3-cephem-4-carboxylic acid, mp 143° to 148° C. (dec). The aqueous layer obtained above was adjusted to pH 1 and extracted with ethyl acetate. The ethyl acetate layer was concentrated to give the crude product (0.01 g) of the same compound as obtained above.

(13) To a mixture of phosgene (22.6 mole) in methylene chloride (50 ml) was dropwise added at 0°–5° C. under stirring a mixture of 3-thiomorpholinone (1.17 g) and triethylamine (2.02 g) in methylene chloride (20 ml), and the resultant mixture was stirred at 0°–5° C. for 4 hours. After removal of the solvent, the residue containing 3-oxo-4-thiomorpholinecarbonyl chloride was dissolved in benzene and an insoluble substance was filtered off. After removal of the solvent, the residue was dissolved in methylene chloride (10 ml) and the resultant solution was dropwise added at 0°–5° C. with stirring to a solution of 7-(D-2-phenylglycinamido)-3-(1-methyl-1H-tetrazol-5-ylthiomethyl)-3-cephem-4-carboxylic acid (2.5 g) and bis(trimethylsilyl)acetamide(3.6 g) in methylene chloride (70 ml). The resultant mixture was stirred at 0°–5° C. for 1.5 hours and concentrated to 20 ml of its volume. The residue was added into a mixture of ethyl acetate (250 ml) and 5% hydrochloric acid (100 ml) under stirring. The ethyl acetate layer was washed with 5% hydrochloric acid and then water and dried over magnesium sulfate. After removal of the solvent, the residue was pulverized with diethyl ether, and the resultant powder (3.05 g) was dissolved in a 5% sodium bicarbonate aqueous solution (100 ml). The aqueous solution was washed with ethyl acetate (100 ml and then 50 ml), and layered with diethyl ether (200 ml). The resultant mixture was adjusted to pH 4 with 10% hydrochloric acid. An insoluble substance (1.48 g) was collected by filtration and dissolved in a mixture of ethyl acetate and diethyl ether. After removal of the solvent, the residue was pulverized with diethyl ether to give powder (1.05 g) of 7-[D-2-(3-oxo-4-thiomorpholinecarboxamido)-2-phenylacetamido]-3-(1-methyl-1H-tetrazol-5-ylthiomethyl)-3-cephem-4-carboxylic acid, mp 151° to 155° C. (dec). The aqueous layer obtained above was added with ethyl acetate (100 ml) and adjusted to pH 1 with 10% hydrochloric acid under stirring. The ethyl acetate layer was concentrated to give the crude product (0.28 g) of the same compound as obtained above.

(14) Powder (130 mg) of 7-[D-2-(2-methylthio-5-oxo-5,6-dihydro-4H-1,3,4-thiadiazine-4-carboxamido)-2-phenylacetamido]-3-(1-methyl-1H-tetrazol-5-ylthiomethyl)-3-cephem-4-carboxylic acid, mp 128° to 134° C. (dec) (reprecipitated with a mixture of ethyl acetate and diethyl ether) was obtained in a similar manner to that of Example (1-11), by reacting 2-methylthio-5-oxo-5,6-dihydro-4H-1,3,4-thiadiazine-4-carbonyl chloride, which was prepared from 2-methylthio-5,6-dihydro-4H-1,3,4-thiadiazin-5-one (150 mg), phosgene (0.0026 mole) and triethylamine (200 mg) in tetrahydrofuran, with a solution of 7-(D-2-phenylglycinaimido)-3-(1-methyl-1H-tetrazol-5-ylthiomethyl)-3-cephem-4-carboxylic acid (400 mg) and bis(trimethylsilyl)acetamide (600 mg) in methylene chloride.

(15) Powder (2.02 g) of 7-[D-2-(2-oxo-5-methylthio-2,3-dihydro-1,3,4-thiadiazole-3-carboxamido)-2-phenylacetamido]-3-(1-methyl-1H-tetrazol-5-ylthiomethyl)-3-cephem-4-carboxylic acid, mp 146° to 150° C. (dec) was obtained in a similar manner to that of Example (1-11), reacting 2-oxo-5-methylthio-2,3-dihydro-1,3,4-thiadiazole-3-carbonyl chloride, which was prepared a mixture of 5-methylthio-2,3-dihydro-1,3,4-thiadiazol-2-one (1.18 g) in tetrahydrofuran (40 ml), phosgene (0.018 mole) and triethylamine (1.6 g) in tetrahydrofuran (7 ml), with a solution of 7-(D-2-phenylglycinamido)-3-(1-methyl-1H-tetrazol-5-thiomethyl)-3-cephem-4-carboxylic acid (3.5 g) and bis(trimethylsilyl)acetamide (5.6 g) in methylene chloride (70 ml).

(16) To a solution of 7-(D-2-phenylglycinamido)-3-(1-methyl-1H-tetrazol-5-ylthiomethyl)-3-cephem-4-carboxylic acid (2.5 g) and bis(trimethylsilyl)acetamide (6 ml) in methylene chloride (100 ml) was bit-by-bit added at −20° C. with stirring powder (1.7 g) of 2-imino-4-oxo-1,2,3,4-tetrahydopyrimidin-6-ylacetyl chloride hydrochloride. The resultant mixture was stirred up to room temperature for an hour and further stirred for another hour at room temperature. After removal of the solvent, the residue was dissolved in water and an insoluble substance was collected by filtration and washed with ethyl acetate to give powder (2.8 g). Thus obtained powder (2.4 g) was dissolved in an aqueous solution (24 ml) consisting of two parts of hydrochloric acid and one part of water under cooling, and active charcoal (0.8 g) was added thereto. The resultant mixture was stirred for 10 minutes and filtered. The filtrate was adjusted to pH 3 with a conc. ammonia aqueous solution and the precipitates which separated were collected by filtration. Thus obtained precipitates were washed with water, ethyl acetate and diethyl ether in turn and dried to give a solid (1.4 g) of 7-[D-2-(2-imino-4-oxo-1,2,3,4-tetrahydropyrimidin-6-ylacetamido)-2-phenylacetamido]-3-(1-methyl-1H-tetrazol-5-ylthiomethyl)-3-cephem-4-carboxylic acid, mp 200° to 205° C. (dec).

(17) In a similar manner to that of Example (1-16), 2-oxo-5-methyl-2,3-dihydro-1,3,4-oxadiazole-3-carbonyl chloride (230 mg) in methylene chloride (3 ml) was treated with a solution of 7-(D-2-phenylglycinamido)-3-(1-methyl-1H-tetrazol-5-ylthiomethyl)-3-cephem-4-carboxylic acid (600 mg) and bis(trimethylsilyl)acetamide (1.0 g) in methylene chloride (20 ml). The reaction mixture was worked up a similar manner to that of Example (1-11) to give powder (410 mg), which was reprecipitated with a mixture of acetone and ethyl acetate to give powder (300 mg) of 7-[D-2-(2-oxo-5-methyl-2,3-dihydro-1,3,4-oxadiazole-3-carboxamido)-2-phenylacetamido]-3-(1-methyl-1H-tetrazol-5-ylthiomethyl)-3-cephem-4-carboxylic acid, mp 145° to 150° C. (dec).

(18) In a similar manner to that of Example (1-16), 1-phenyl-5-oxo-4,5-dihydro-1H-1, 2,3-triazole-4-carbonyl chloride (2.23 g) in methylene chloride (22 ml), was treated with a solution of 7-(D-2-phenylglycinamido)-3-(1-methyl-1H-tetrazol-5-ylthiomethyl)-3-cephem-4-carboxylic acid (5.06 g) and bis(trimethylsilyl) acetamide (8.0 g) in methylene chloride (150 ml). The reaction mixture was concentrated and to the residue was added ethyl acetate (250 ml) and 5% hydrochloric acid (70 ml). The organic layer was washed with an aqueous solution of sodium chloride, dried over magnesium and concentrated to about 10 ml of its volume. To the residue was added diethyl ether and an insoluble substance (3.82 g) was collected by filtration. The filtrate was concentrated and diethyl ether was added to the residue (1.38 g). An insoluble substance (310 mg) was collected by filtration and combined together with the insoluble substance (3.82 g) obtained above. Thus obtained substance was washed with diethyl ether and dissolved in a mixture of acetic acid (4 ml) and ethyl acetate (10 ml) and subjected to column chromatography on silica gel. The fraction containing the designated product was concentrated and the residue (1.09 g) was dissolved in an aqueous solution of sodium bicarbonate. Ethyl acetate was added to the solution and the mixture was adjusted to pH 4 with 10% hydrochloric acid under stirring. The aqueous layer was separated and adjusted to pH 2 with 10% hydrochloric acid to give powder (860 mg) of 7-[D-2-(1-phenyl-5-oxo-4,5-dihydro-1H-1,2,3-triazole-4-carboxamido)-2-phenylacetamido]-3-(1-methyl-1H-tetrazol-5-ylthiomethyl)-3-cephem-4-carboxylic acid, mp 180° to 192° C. (dec).

(19) In a similar manner to that of Example (1-16), 2-(2-pyridyloxy)acetyl chloride hydrochloride (2.49 g) was treated with a solution of 7-(D-2-phenylglycinamido)-3-(1-methyl-1H-tetrazol-5-ylthiomethyl)-3-cephem-4-carboxylic acid (3.0 g) and bis(trimethylsilyl)acetamide (6.0 g) in methylene chloride (80 ml). Thus obtained reaction mixture was concentrated, and to the residue was added ethyl acetate (70 ml) and 5% sodium bicarbonate aqueous solution (50 ml), and the resultant mixture was stirred at room temperature for 15 minutes. An insoluble substance was collected by filtration, suspended in water (30 ml) and, after addition of ethyl acetate, the mixture was adjusted to pH 2 with 10% hydrochloric acid. The organic layer was washed with water, dried over magnesium sulfate and concentrated. The residue was triturated with diethyl ether, and the resultant powder (1.75 g) was reprecipitated with a mixture of acetone and water to give powder of 7-{D-2-[2-pyridyloxy)acetamido]-2-phenylacetamido}-3-(1-methyl-1H-tetrazol-5-ylthiomethyl)-3-cephem-4-carboxylic acid, mp 127° to 132° C. (dec). The aqueous layer of the filtrate mentioned above was layered with ethyl acetate and adjusted to pH 2 with 10% hydrochloric acid. The aqueous layer was separated and extracted with ethyl acetate. The ethyl acetate extract was washed with water, dried over magnesium sulfate and then concentrated. The residue was pulverized with diethyl ether to give powder (0.47 g) of the crude product of the same compound as obtained above.

(20) In a similar manner to that of Example (1-16), 3-oxo-6-chloro-2,3-dihydro-4-pyridazinecarbonyl chloride (0.57 g) was treated with a solution of 7-(D-2-phenylglycinamido)-3-(1-methyl-1H-tetrazol-5-ylthiomethyl)-3-cephem-4-carboxylic acid (1.38 g) and bis(-trimethylsilyl)acetamide (2.4 g) in methylene chloride (30 ml). The reaction mixture was treated in a similar manner to that of Example (1-1) to give powder (1.5 g) of 7-[D-2-(3-oxo-6-chloro-2,3-dihydro-4-pyridazinecarboxamido)-2-phenylacetamido]-3-(1-methyl-1H-tetrazol-5-ylthiomethyl)-3-cephem-4-carboxylic acid, mp 153° to 155° C. (dec) (reprecipitated with acetone).

(21) In a similar manner to that of Example (1-16), a solution of 7-(D-2-phenylglycinamido)-3-(5-methyl-1,3,4-thiadiazol-2-ylthiomethyl)-3-cephem-4-carboxylic acid formate (2.62 g), bis(trimethylsilyl)acetamide (5 g) in methylene chloride (30 ml) was treated with a solution of 2,4-dioxo-1,2,3,4-tetrahydro-6-pyrimidinecarbonyl chloride (0.965 g) in methylene chloride (50 ml). The reaction mixture was concentrated under reduced pressure. To the residue was added ethyl acetate and water and the resultant mixture was stirred. The precipitated gummy substance was separated out and pulverized with water. The obtained powder was washed with water and dissolved in 10% aqueous acetone, and an insoluble substance was filtered off. The filtrate was treated with active charcoal and concentrated. The resultant was pulverized with water and the resultant powder was washed with ethanol and diethyl ether to give powder (1.1 g) of 7-[D-2-(2,4-dioxo-1,2,3,4-tetrahydro-6-pyrimidinecarboxamido)-2-phenylacetamido]-3-(5-methyl-1,3,4-thiadiazol-2-ylthiomethyl)-3-cephem-4-carboxylic acid, mp 195° to 200° C. (dec).

(22) To a mixture of 2-(2-pyridyloxy)acetic acid hydrochloride (1.5 g) and acetyl chloride (8 ml) was added at −30° C. phosphorus pentachloride (3.3 g), and the mixture was stirred at room temperature for 18 hours. Precipitated crystals were collected by filtration and washed with a small amount of acetyl chloride and diethyl ether and dried to give 2-(2-pyridyloxy)acetyl chloride (1.3 g). A mixture of 7-(D-2-phenylglycinamido)-3-methyl-3-cephem-4-carboxylic acid (2.5 g) and trimethylsilylacetamide (0.0288 mole) in methylene chloride (70 ml) was stirred for 1.5 hours. The solution was cooled to 3° C. and the above obtained 2-(2-Pyridyloxy)acetyl chloride was added thereto. The resultant mixture was stirred under ice-cooling for 2 hours and concentrated. To the residue was added ice-water and the resultant powder was filtrated and washed with acetone containing water and acetone in turn to give powder (1.4 g). The filtrate and washings were collected together and extracted with ethyl acetate four times. The ethyl acetate extracts were washed with water, dried and concentrated to give powder (0.4 g). Thus obtained powders (1.4 g) and (0.4 g) were combined together and recrystallized from methanol to give crystals (0.9 g) of 7-{D-2-[2-(2-pyridyloxy)acetamido]-2-phenylacetamido}-3-methyl-3-cephem-4-carboxylic acid, mp 209° to 211° C. (dec).

(23) To a solution of 7-(D-2-phenylglycinamido)-3-(5-methyl-1,3,4-thiadiazol-2-ylthiomethyl)-3-cephem-4-carboxylic acid formate (1.57 g), sodium bicarbonate (0.63 g) in water (30 ml) and acetone (30 ml), was dropwise added at 0°-5° C. a solution of 2-phthalimidoacetyl chloride (0.666 g) in acetone (5 ml) and the resultant mixture was stirred at 0°-5° C. for 30 minutes. Precipitates were collected by filtration and washed with water to give sodium 7-[D-2-(2-phthalimidoacetamido)-2-phenylacetamido]-3-(5-methyl-1,3,4-thiadiazol-2-ylthiomethyl)-3-cephem-4-carboxylate (1.15 g), mp 160° to 170° C. (dec).

(24) To a solution of 7-(D-2-phenylglycinamido)-3-(1-methyl-1H-tetrazol-5-ylthiomethyl)-3-cephem-4-carboxylic acid (2.5 g) and sodium bicarbonate (840 mg) in water (50 ml) and acetone (50 ml) was dropwise added under ice-cooling and stirring a solution of 2-(2-amino-4-thiazolyl)acethyl chloride hydrochloride (1.27 g) in dry acetone (10 ml) with keeping the resultant mixture at pH 7.5 to 8 with 5% sodium carbonate. The mixture was stirred at the same temperature for an hour and adjusted to pH 7 with 10% hydrochloric acid. After removal of the solvent, a precipitated substance was collected by filtration and the filtrate was subjected to further treatment described later. Thus obtained precipitate was washed with ethyl acetate and dissolved in water (15 ml) and an aqueous solution (5 ml) containing sodium bicarbonate (420 mg). The resultant solution was stirred with active charcoal under ice-cooling for 15 minutes. After filtrating, the filtrate was adjusted to pH 3 with 10% hydrochloric acid. Precipitats were collected by filtration, washed with water and then ethyl acetate, and suspended in acetone. The suspension was stirred and the precipitates were collected by filtration and washed with diethyl ether and petroleum ether and dried to give a solid (0.7 g) of 7-{D-2-[2-(2-amino-4-thiazolyl)acetamido]-2-phenylacetamido}-3-(1-methyl-1H-tetrazol-5-ylthiomethyl)-3-cephem-4-carboxylic acid, mp 185° to 190° C. (dec). The filtrate obtained above was layered with ethyl acetate and adjusted to pH 4 with 10% hydrochloric acid. The aqueous layer was subjected to column chromatography on Amberlite XAD-2 (prepared by Rohm and Haas Co) and eluted with methanol. The methanol fraction was concentrated and the residue was triturated with acetone. The precipitats were collected by filtration and washed with diethyl ether to give the same product as obtained above.

(25) To a solution of 7-(D-2-phenylglycinamido)-3-(1-methyl-1H-tetrazol-5-ylthiomethyl)-3-cephem-4-carboxylic acid (2.5 g) and sodium bicarbonate (1.26 g) in acetone (70 ml) and water (70 ml) was dropwise added under ice-cooling and stirring a solution of 2-amino-4-thiazolecarbonyl chloride hydrochloride (8 m mole) in dry acetone (20 ml) with keeping the resultant mixture at pH 7.5 to 8 with 5% sodium carbonate. After removal of the solvent, the residue was cooled and precipitates were collected by filtration and dried to give powder (2.68 g). Thus obtained powder (2.5 g) was dissolved in acetone (25 ml) and water (12.5 ml) and active charcoal was added thereto, and the mixture was stirred for 20 minutes. After removal of the active charcoal, the filtrate was concentrated and cooled. Separated precipitates were collected by filtration and washed with a small amount of water and suspended in a mixture of acetone (30 ml) and water (2 drops). The resultant mixture was stirred for 1.5 hours, and the solid was collected by filtration, washed with water and dried to give powder (0.9 g) of 7-[D-2-(2-amino-4-thiazolecarboxamido)-2-phenylacetamido]-3-(1-methyl-1H-tetrazol-5-ylthiomethyl)-3-cephem-4-carboxylic acid, mp 185° to 190° C. (dec).

(26) To a solution of 7-(D-2-phenylglycinamido)-3-(5-methyl-1,3,4-thiadiazol-2-ylthiomethyl)-3-cephem-4-carboxylic acid formate (3.1 g) and sodium bicarbonate (1.5 g) in water (100 ml) and acetone (100 ml) was dropwise added under ice-cooling and stirring 2,3-pyrazinedicarboxylic anhydride (1.0 g) and the resultant mixture was stirred for 1.5 hours at the same temperature. The reaction mixture was concentrated and washed with ethyl acetate. The aqueous layer was added with a mixture of ethyl acetate (100 ml) and acetone (50 ml) and then adjusted pH 2 with 10% hydrochloric acid. The organic layer was separated out for further treatment and the aqueous layer was extracted twice with a mixture of ethyl acetate (50 ml) and acetone (10 ml). The organic layers obtained here and in the above were joined together, washed with an aqueous solution of sodium chloride, dried over magnesium sulfate, and concentrated. The residue was pulverized with diethyl ether to give powder (2.8 g). Thus obtained powder (2.5 g) was treated with active carbon in acetone and filtered. The filtrate was concentrated, and the residue was pulverized with diethyl ether to give powder (2.0 g) of 7-[D-2-(3-carboxy-2-pyrazinecarboxamido)-2-phenylacetamido]-3-(5-methyl-1,3,4-thiadiazol-2-ylthiomethyl)-3-cephem-4-carboxylic acid, mp 167° to 170° C. (dec).

(27) To a mixture of 2-β-methyl-5-oxo-4,5-dihydro-1H-1,2,4-triazol-4-yl) acetic acid (156 mg), triethylamine (100 mg) and N,N-dimethyl-N-benzylamine (a few drops) in methylene chloride (10 ml), was dropwise added at −10° to −15° C. under stirring a mixture of pivaloyl chloride (120 mg) in methylene chloride (1 ml) and the resultant mixture was stirred at the same temperature for an hour. To the reaction mixture containing 2-(3-methyl-5-oxo-4,5-dihydro-1H-1,2,4-triazol-4-yl)acetic pivalic anhydride was added at −30° C. a solution of 7-(D-2-phenylglycinamido)-3-(1-methyl-1H-tetrazol-5-ylthiomethyl)-3-cephem-4-carboxylic acid (500 mg) and bis(trimethylsilyl)acetamide (800 mg) in methylene chloride (10 ml), and the resultant mixture was stirred at −20° to −30° C. for 15 minutes, −10° to −15° C. for 2 hours and 0° to 5° C. for an hour, and concentrated. The residue was added with ethyl acetate (3 ml) and 5% hydrochloric acid (30 ml). An insoluble substance was collected by filtration and washed with water to give powder (320 mg) of 7-{D-2-[2-(3-methyl-5-oxo-4,5-dihydro-1H-1,2,4-triazol-4-yl)acetamido]-2-phenylacetamido}-3-(1-methyl-1H-tetrazol-5-ylthiomethyl)-3-cephem-4-carboxylic acid, mp 168° to 175° C. (dec). The ethyl acetate layer was concentrated also to give crude powder (240 mg) of the same product.

(28) To a solution of isobutyl chloroformate (0.822 g) in methylene chloride (60 ml) was dropwide added at −10° to −15° C. a mixture of 2-(2-thioxo-4-methyl-2,3-dihydro-3-thiazolyl)acetic acid (1.134 g), N,N-dimethyl-N-benzylamine (a few drops) and triethylamine (0.6 g) in methylene chloride (30 ml) and the resultant mixture was stirred at the same temperature for 30 minutes. To the reaction mixture containing 2-(2-thioxo-4-methyl-2,3-dihydro-3-thiazolyl)acetic isobutyloxycarboxylic anhydride, was added a solution of 7-(D-2-phenylglycinamido)-3-(1-methyl-1H-tetrazol-5-ylthiomethyl)-3-cephem-4-carboxylic acid (2.77 g) and bis(trimethylsilyl)acetamide (4.8 g) in methylene chloride (60 ml) and the resultant mixture was stirred at −10° to −20° C. for 2 hours and at 0° to 5° C. for another 2 hours. Thus obtained reaction mixture was concentrated, and the residue was added with ethyl acetate and water. The mixture was adjusted to pH 1 with 10% hydrochloric acid. An insoluble substance was filtered off and the ethyl acetate layer was added with an aqueous solution of sodium bicarbonate. Precipitates were collected by filtration and suspended in water and the suspension was adjusted to pH 1 and stirred for an hour to give powder (1.8 g) of 7-{D-2-[2-(2-thioxo-4-methyl-2,3-dihydro-3-thiazolyl) acetamido]-2-phenylacetamido}-3-

(1-methyl-1H-tetrazol-5-ylthiomethyl)-3-cephem-4-carboxylic acid, mp 150° to 155° C.

(29) A mixture of 2-(3-hydroxy-6-oxo-1,6-dihydro-1-pyridazinyl)acetic acid (2.04 g), triethylamine (1.20 g) and N,N-dimethyl-N-benzylamine (trace) in methylene chloride (60 ml) was dropwise added at −10° to −15° C. to a solution of isobutyl chloroformate (1.64 g) in methylene chloride (60 ml) and the resultant mixture was stirred for an hour at the same temperature. The reaction mixture containing 2-(3-hydroxy-6-oxo-1,6-dihydro-1-pyridazinyl)acetic isobutyloxycarboxylic anhydride was added at −40° C. to a solution of 7-(D-2-phenylglycinamido)-3-(1-methyl-1H-tetrazol-5-ylthiomethyl)-3-cephem-4-carboxylic acid (3.0 g) and bis(trimethylsilyl)acetamide (4.8 g) in methylene chloride (60 ml). The resultant mixture was stirred at −10° to −20° C. for 2 hours, under ice-cooling for an hour and then at room temperature for another one hour, after which the solvent was removed. The residue was added to ethyl acetate (150 ml) and 5% hydrochloric acid (100 ml). The ethyl acetate layer was washed with water and concentrated. The residue was pulverized with diethyl ether. The resultant powder (2.08 g) was dissolved in an aqueous solution of sodium bicarbonate and adjusted to pH 2 with 10% hydrochloric acid. Precipitates were collected by filtration to give powder (1.22 g) of 7-{D-2-[2-(3-hydroxy-6-oxo-1,6-dihydro-1-pyridazinyl)acetamido]-2-phenylacetamido}-3-(1-methyl-1H-tetrazol-5-ylthiomethyl)-3-cephem-4-carboxylic acid, mp 168° to 171° C. (dec).

(30) A mixture of 2-(1,6-dimethyl-4-oxo-1,4-dihydropyridin-3-yloxy)acetic acid (1.97 g) and triethylamine (10 ml) in methylene chloride (100 ml) was stirred at room temperature for 20 minutes. The resultant solution was concentrated and methylene chloride (100 ml) was added to the residue. The mixture was cooled to 0° C., and a solution of thionyl chloride (1.2 g) in methylene chloride (10 ml) was dropwise added thereto. The resultant mixture was stirred at the same temperature for 30 minutes. A solution of 7-(D-2-phenylglycinamido)-3-(1-methyl-1H-tetrazol-5-ylthiomethyl)-3-cephem-4-carboxylic acid (5.0 g) and bis(trimethylsilyl)acetamide in methylene chloride (150 ml) cooled at 0° C. was added to the above obtained reaction mixture containing 2-(1,6-dimethyl-4-oxo-1,4-dihydropyridin-3-yloxy)acetyl chloride. The resultant mixture was stirred up to room temperature for an hour. The reaction mixture was concentrated and water (200 ml) was added to the residue. The mixture was stirred and precipitates were collected by filtration, washed with water and dissolved in a mixture of water and 5% sodium bicarbonate, whereby the solution was adjusted to pH 8. The solution was adjusted to pH 5 to 6 with 10% hydrochloric acid. An insoluble substance was filtered off, and the filtrate was treated with active charcoal (1 g) and adjusted to pH 1 to 2 with 10% hydrochloric acid. The resulting precipitates were collected by filtration and dried to give crystals (3.5 g), which were washed with acetone (100 ml) and then with water (100 ml) under stirring, collected by filtration, washed with water and dried to give crystals (1.5 g) of 7-{D-2-[2-(1,6-dimethyl-4-oxo-1,4-dihydropyridin-3-yloxy)acetamido]-2-phenylacetamido}-3-(1-methyl-1H-tetrazol-5-ylthiomethyl)-3-cephem-4-carboxylic acid, mp 168° to 173° C. (dec).

(31) To a mixture of 2-(4-oxo-5-chloro-6-methyl-1,4-dihydropyridin-3-yloxy)acetic acid (2.17 g) in methylene chloride (50 ml) was added triethyl amine (1.01 g) under stirring at room temperature. The resultant mixture was stirred for 20 minutes, a solution of thionyl chloride (1.2 g) in methylene chloride (2 ml) was added dropwise thereto under ice-cooling and the mixture was stirred for 30 minutes. To the reaction mixture containing activated 2-(4-hydroxy-5-chloro-6-methylpyridin-3-yloxy)acetic acid was added at 0° C. a solution of 7-(D-2-phenylglycinamido)-3-(1-methyl-1H-tetrazol-5-ylthiomethyl)-3-cephem-4-carboxylic acid (4.56 g) and bis(trimethylsilyl)acetamido (9 ml) in methylene chloride (120 ml). The resultant mixture was stirred at 0° C. for 30 minutes, at a gradually elevated temperature and then at room temperature for 2.5 hours. After removal of the solvent, to the residue was added water (100 ml). The aqueous suspension was adjusted to pH 2 with 10% hydrochloric acid and ethyl acetate (200 ml) was added thereto. The resultant precipitates were washed with water and dissolved in water by addition of a 5% sodium bicarbonate aqueous solution. The solution was adjusted to pH 3–4 with 10% hydrochloric acid and separated precipitates were filtered. The filtrate was adjusted to pH 1–2 with 10% hydrochloric acid to give powder. On the other hand, the precipitates were dissolved in an aqueous sodium bicarbonate solution, and the aqueous solution was adjusted to pH 5–6 with 10% hydrochloric acid, and filtered. The filtrate was further adjusted to pH 1–2 with 10% hydrochloric acid to give powder. Thus obtained powders were combined together, dissolved in a 3% sodium bicarbonate aqueous solution, and the solution was left standing for a few hours. The resulting suspension was diluted with water (10 ml) and precipitates were collected by filtration, washed with water and dried to give powder (0.73 g) of sodium 7-{D-2-[2-(4-oxo-5-chloro-6-methyl-1,4-dihydropyridin-3-yloxy)acetamido]-2-phenylacetamido}-3-(1-methyl-1H-tetrazol-5-ylthiomethyl)-3-cephem-4-carboxylate, mp 180° to 185° C. (dec).

(32) A mixture of 7-(D-2-phenylglycinamido)-3-methyl-3-cephem-4-carboxylic acid (3.0 g) and trimethylsilylacetamide (0.0348 mole) in methlene chloride (130 ml) was stirred at room temperature for 1.5 hours and filtered. To the filtrate was added nicotinic acid chloride (2.37 g) and the resulting solution was stirred for 30 minutes. An appearing powder was collected by filtration and dissolved in a sodium bicarbonate aqueous solution. The solution was adjusted to pH 3 with 1 N-hydrochloric acid and the resultant powder was collected by filtration and washed to give powder (3.2 g) of 7-(D-2-nicotinamido-2-phenylacetamido)-3-methyl-3-cephem-4-carboxylic acid, mp 183° to 185° C. (dec).

(33) A mixture of picolinic acid (1.85 g), thionyl chloride (18 ml), benzene (9 ml) and dimethylformamide (0.11 g) was heated under reflux for 2 hours. After removal of excess of thionyl chloride, benzene was added to the residue and the resultant solution was concentrated. The residue containing picolinoyl chloride was dissolved in benzene (8 ml), and the resultant solution was dropwise added to a suspension of 7-(D-2-phenylglycinamido)-3-methyl-3-cephem-4-carboxylic acid (3.5 g) in dimethylformamide (50 ml) under ice-cooling. The mixture was stirred at room temperature for 5 hours. The reaction mixture was filtered and the filtrate was concentrated. To the residue was added water, and an insoluble substance was collected by filtration and dissolved in a sodium bicarbonate aqueous solution. The solution was adjusted to pH 2 with 1 N hydrochloric acid and appearing precipitates were collected by filtration and washed with water to give powder (1.95 g) of 7-(D-2-picolinamido-2-phenylacetamido)-3-methyl-3-cephem-4-carboxylic acid, mp 150° to 160° C. (dec).

(34) A mixture of 2-(4-oxo-5-chloro-6-hydroxymethyl-1,4-dihydropyridin-3-yloxy)acetic acid (1.17 g) and triethylamine (15 ml) in methylene chloride (70 ml) was stirred for 30 minutes at room temperature. After evaporation to dryness, methylene chloride (70 ml) was added to the residue, and thionyl chloride (0.6 g) was dropwise added thereto under ice-cooling with stirring. The resultant mixture was stirred for 15 minutes at the same temperature. A solution of 7-(D-2-phenylglycinamido)-3-(1-methyl-1H-tetrazol-5-ylthiomethyl)-3-cephem-4-carboxylic acid (2.0 g) and bis(trimethylsilyl)acetamide (5 ml) in methylene chloride (100 ml) was added at 0° C. to the reaction mixture containing 2-(4-oxo-5-chloro-6-hydroxymethyl-1,4-dihydropyridin-3-yloxy)acetyl chloride. The resultant mixture was stirred up to room temperature for 1.5 hours and the solvent was distilled off. To the residue were added water and 10% hydrochloric acid, whereby the medium was adjusted to pH 1 to 2, and the mixture was stirred to give powder. The powder was dissolved in water and 5% sodium bicarbonate aqueous solution, whereby the solution was adjusted to pH 8 and reprecipitated by adjusting the medium to pH 1 to 2 with 10% hydrochloric acid. To the obtained precipitates was added ethyl acetate, and the resultant mixture was stirred for 30 minutes. Appearing precipitates (1.5 g) collected by filtration were stirred in acetone (50 ml) for 2 hours. The resulting precipitates were collected by filtration, dissolved in hydrous acetone and treated with active charcoal. After removal of the acetone, precipitated crystals were collected by filtration, washed with water and dried to give crystals (0.7 g) of 7-{D-2-[2-(4-oxo-5-chloro-6-hydroxymethyl-1,4-dihydropyridin-3-yloxy)acetamido]-2-phenylacetamido}-3-(1-methyl-1H-tetrazol-5-ylthiomethyl)-3-cephem-4-carboxylic acid, mp 175° to 180° C. (dec).

N.M.R. Spectrum (Acetone-$D_6$+$D_2O$, $\delta$) Internal standard : Trimethylsilan ppm 3.68 (2H, broad s), 4.00 (3H, s), 4.38 (2H, s), 4.66 (2H, s), 4.74 (2H, s), 5.10 (1H, d, J=5 Hz), 5.82 (1H, d, J=5 Hz), 5.82 (1H, s), 7.28 to 7.75 (5H, m), 7.82 (1H, s).

(35) A mixture of 2-(4-oxo-6-chloromethyl-1,4-dihydropyridin-3-yloxy)acetic acid (4.0 g) and triethylamine (10 ml) in methylene chloride (100 ml) was stirred at room temperature and the solvent and excess triethylamine were distilled off from the resultant solution. The residue was dissolved in methylene chloride (200 ml), and thionyl chloride (2.18 g) was added thereto at 0° C. The resultant mixture was stirred at 0° C. for 30 minutes. A solution of 7-(D-2-phenylglycinamido)-3-(1-methyl-1H-tetrazol-5-ylthiomethyl)-3-cephem-4-carboxylic acid (8.9 g) and bis(trimethylsilyl)acetamide (20 g) in methylene chloride (150 ml) was added under ice-cooling to the reaction mixture containing 2-(4-oxo-6-chloromethyl-1,4-dihydropyridin-3-yloxy) acetyl chloride. The resultant mixture was stirred for 30 minutes under ice-cooling and for 2.5 hours at room temperature. The reaction mixture was concentrated and the residue was pulverized with water. Thus obtained powder was suspended in water, and a sodium bicarbonate aqueous solution was added thereto. To the resultant solution was added ethyl acetate and the mixture was adjusted to pH 1 with 10% hydrochloric acid. Appearing precipitates were collected by filtration and washed with water and dry acetone to give powder (3.5 g). Thus obtained powder (2.0 g) was dissolved in a mixture of acetone and water and treated with active charcoal (1.8 g). Removal of the charcoal and acetone gave powder (1.0 g) of 7-{D-2-[2-(4-oxo-6-chloromethyl-1,4-dihydropyridin-3-yloxy)acetamido]-2-phenylacetamido}-3-(1-methyl-1H-tetrazol-5-ylthiomethyl)-3-cephem-4-carboxylic acid, mp 165° to 170° C. (dec).

N.M.R. Spectrum (Acetone-$D_6$, $\delta$) Internal standard : Trimethylsilan ppm 2.65 (2H, ABq, J=18 Hz), 4.00 (3H, s), 4.70 (4H, s), 5.08 (1H, d, J=5 Hz), 5.78 (1H, d, J=5 Hz), 5.80 (1H, s), 6.75 (1H, s), 7.2 to 7.7 (5H, m), 7.88 (1H, s).

(36) A mixture of 2-(4-oxo-6-methyl-1,4-dihydropyridin-3-yloxy)acetic acid (915 mg) and triethylamine (5 ml) in methylene chloride (50 ml) was stirred at room temperature for 30 minutes. After evaporation to dryness, methylene chloride (50 ml) was added to the residue. To the resultant solution was added dropwise thionyl chloride (600 mg) with stirring under ice-cooling. Thus obtained mixture was stirred for 30 minutes at the same temperature, and a solution of 7-(D-2-phenylglycinamido)-3-(1-methyl-1H-tetrazol-5-ylthiomethyl)-3-cephem-4-carboxylic acid (2.5 g) and bis(trimethylsilyl)acetamide (5 ml) in methylene chloride (100 ml) was added at 0° C. to the reaction mixture containing activated 2-(4-oxo-6-methyl-1,4-dihydropyridin-3-yloxy)acetic acid. The resultant mixture was stirred up to room temperature for an hour. After removal of the solvent, the residue was added to water (100 ml) and stirred for an hour. The resulting precipitates were collected by filtration, washed with water and dissolved in a mixture of acetone (50 ml) and water (10 ml). The obtained solution was treated with active charcoal and the acetone was distilled off. To the residue was added water (10 ml) and the resultant mixture was stirred for 30 minutes. The resulting crystals were collected by filtration, washed with water and dried to give crystals (1.6 g) of 7-{D-2-[2-(4-oxo-6-methyl-1,4-dihydropyridin-3-yloxy)acetamido]-2-phenylacetamido}-3-(1-methyl-1H-tetrazol-5-ylthiomethyl)-3-cephem-4-carboxylic acid, mp 170° to 175° C. (dec).

N.M.R. Spectrum (Acetone-$D_6$+$D_2O$, $\delta$) Internal standard : Trimethylsilan ppm 2.40 (3H, s), 3.66 and 3.74 (2H, ABq, J=17 Hz), 4.00 (3H, s), 4.38 (2H, s), 4.68 (2H, s), 5.10 (1H, d, J=4 Hz), 5.80 (1H, d, J=4 Hz), 5.83 (1H, s), 6.60 (1H, s), 7.28 to 7.69 (5H, m), 7.85 (1H, s).

(37) A mixture of 2-(4-oxo-5-chloro-6-methyl-1,4-dihydropyridin-3-yloxy)acetic acid dihydrate (1.95 g) and triethylamine (4.5 ml) in methylene chloride (100 ml) was stirred at room temperature for 15 minutes. After evaporation to dryness, methylene chloride (100 ml) was added to the residue, and the mixture was stirred under ice-cooling. Thionyl chloride (1.08 g) in methylene chloride (5 ml) was dropwise added thereto, and the resultant mixture was stirred for 15 minutes under ice-cooling. A solution of 7-[D-2-(4-hydroxyphenyl)glycinamido]-3-(1-methyl-1H-tetrazol-5-ylthiomethyl)-3-cephem-4-carboxylic acid (3.5 g) and bis(trimethylsilyl)acetamide (10 ml) in methylene chloride (100 ml) was added at 0° C. to the reaction mixture containing activated 2-(4-oxo-5-chloro-6-methyl-1,4-dihydropyridin-3-yloxy)acetic acid. The resultant mixture was stirred at 0° C. for 2 hours and at room temperature for 2 hours. The solvent was distilled off and to the residue were added water and then 10% hydrochloric acid to adjust it to pH 1 to 2, and the obtained mixture was stirred. The resulting precipitates (3 g) were collected by filtration and suspended in a mixture of water and ethyl acetate. The suspension was adjusted to pH 7.5 to 8 with an aqueous sodium bicarbonate solution, stirred and then adjusted to pH 5 with 10% hydrochloric acid. An insoluble substance was filtered off and the filtrate was adjusted to pH 1 to 2 with 10% hydrochloric acid. Appearing precipitates were collected by filtration, washed with water and ethyl acetate and dried to give crystals (1.8 g). These crystals were dissolved in hydrous acetone and treated with active charcoal (2 g). The solvent was distilled off, and precipitated crystals were collected by filtration, washed with water and dried to give crystals (0.8 g) of 7-{D-2-[2-(4-oxo-5-chloro-6-methyl-1,4-dihydropyridin-3-yloxy)acetamido]-2-(4-hydroxy)phenylacetamido}-3-(1-methyl-1H-tetrazol-5-ylthiomethyl)-3-cephem-4-carboxylic acid, mp 180° to 185° C. (dec), which was analysed by Karl-Fisher's method to reveal about 2 molar equivalent water.

N.M.R. Spectrum (Acetone-$D_6$+$D_2O$, δ) Internal standard : Trimethylsilan ppm 2.46 (3H, s), 3.66 (2H, broad s), 4.00 (3H, s), 4.36 (2H, s), 4.58 (2H, s), 5.07 (1H, d, J=4 Hz), 5.70 (1H, s), 5.80 (1H, d, J=4 Hz), 6.84 (2H, d, J=8 Hz), 7.40 (2H, d, J=8 Hz), 7.71 (1H, s).

(38) A mixture of 2-(4-oxo-1,4-dihydropyrimidin-5-yloxy)acetic acid (850 mg) and triethylamine (5 ml) in methylene chloride (100 ml) was stirred at room temperature for 30 minutes. After evaporation to dryness, methylene chloride (100 ml) was added to the residue, and thionyl chloride (600 mg) in methylene chloride (2 ml) was dropwise added thereto under ice-cooling with stirring, after which the resultant mixture was stirred at the same temperature for 30 minutes. A solution of 7-(D-2-phenyl-glycinamido)-3-(1-methyl-1H-tetrazol-5-ylthiomethyl)-3-cephem-4-carboxylic acid (2.2 g) and bis(trimethylsilyl)acetamide (5 ml) in methylene chloride (100 ml) was added at 0° C. to the reaction mixture containing 2-(4-oxo-1,4-dihydropyrimidin-5-yloxy)acetic acid. The resultant mixture was stirred up to room temperature for 1.5 hours and the solvent was distilled off. To the residue was added water and the resultant aqueous mixture was stirred to give powder. Thus obtained powders was collected by filtration, dissolved in a mixture of water and 5% sodium bicarbonate aqueous solution, whereby the solution was adjusted to pH 8, and then reprecipitated by adjusting the solution to pH 2 with 10% hydrochloric acid. The resulting precipitates were collected by filtration and dried. Thus obtained powder (2.0 g) was stirred in ethyl acetate (100 ml) and collected by filtration. Thus obtained crystals (1.65 g) were dissolved in acetone (5 ml) and water (10 ml) and treated with active charcoal (2.0 g). After removal of the solvent, the resulting crystals were collected by filtration, washed with water and dried to give crystals (1.2 g). The aqueous filtrates and washings were combined and treated similarly to give an additional amount of crystals (0.4 g) of 7-{D-2-[2-(4-oxo-1,4-dihydropyrimidin-5-yloxy)acetamido]-2-phenylacetamido}-3-(1-methyl-1H-tetrazol-5-ylthiomethyl)-3-cephem-4-carboxylic acid, m.p. 170° to 175° C. (dec).

N.M.R. Spectrum (Acetone-$D_6$+$D_2O$, δ) Internal standard : Trimethylsilan ppm 3.70 (2H, broad s), 4.00 (3H, s), 4.40 (2H, s), 4.72 (2H, s), 5.08 (1H, d, J=5 Hz), 5.35 (1H, d, J=5 Hz), 5.35 (1H, s), 7.25 to 7.70 (5H, m), 7.78 (1H, s), 8.10 (1H, s).

(39) A mixture of potassium 2-(2-oxo-1,2-dihydropyrazin-1-yloxy)acetate (3.1 g) in dry benzene (100 ml) was stirred at 10° C. Oxalyl chloride (5 ml) and then dimethylformamide (3 drops) were added thereto and the resultant mixture was stirred for 1.5 hours at room temperature. After evaporation to dryness, methylene chloride was added to the residue, and the resultant mixture was cooled at 0° C. A solution of 7-(D-2-phenylglycinamido)-3-(1-methyl-1H-tetrazol-5-ylthiomethyl)-3-cephem-4-carboxylic acid (5.5 g) and bis(trimethylsilyl)acetamide (11 ml) in methylene chloride (150 ml) was added at 0° C. to the reaction mixture containing 2-(2-oxo-1,2-dihydropyrazin-1-yloxy)acetyl chloride. The mixture was stirred up to room temperature for an hour and the solvent was distilled off. To the residue was added water (200 ml) with stirring to pluverize it. The resulting precipitates were washed with water, dissolved in a mixture of acetone (100 ml) and water (10 ml) and treated with active charcoal (3 g). After removal of the acetone, the aqueous layer was separated out by decantation, and oil was washed with water and dissolved in a 5% sodium bicarbonate aqueous solution. The solution was adjusted to pH 2, and appearing precipitates (3.5 g) were collected by filtration, washed with water and dried. The resultant powder was stirred in acetone (100 ml) for an hour and an insoluble substance was filtered off. The filtrate was concentrated to the volume of 30 ml, to which ether was added. The resulting precipitates were washed with ether, dissolved in acetone and treated with active charcoal. After removal of the acetone, the residue was dissolved in a mixture of water and 5% sodium bicarbonate aqueous solution, whereby the solution is adjusted to pH 8, and reprecipitated with 10% hydrochloric acid. The resulting precipitates were collected by filtration, washed with water and dried to give crystals (1.5 g) of 7-{D-2-[2-(2-oxo-1,2-dihydropyrazin-1-yloxy)acetamido]-2-phenylacetamido}-3-(1-methyl-1H-tetrazol-5-ylthiomethyl)-3-cephem-4-carboxylic acid, mp 120° to 125° C. (dec).

N.M.R. Spectrum (Acetone-$D_6$+$D_2O$, δ) Internal standard : Trimethylsilan ppm 3.65 (2H, s), 3.95 (3H, s), 4.40 (2H, s), 4.95 (2H, s), 5.05 (1H, d, J=5 Hz), 5.90 (1H, d, J=5 Hz), 5.80 (1H, s), 7.20 to 7.60 (6H, m), 7.98 (1H, d, J=6 Hz), 8.15 (1H, s).

(40) A mixture of 2-(4-thioxo-6-methyl-4H-pyran-3-yloxy)acetic acid (1.0 g) in methylene chloride (100 ml) was stirred at −20° C., and isobutyl chlorocarbonate (1.3 g) was added thereto. The resultant mixture was stirred for 5 minutes and triethylamine (1.0 g) was dropwise added thereto and the resultant mixture was stirred for 15 minutes. A solution of 7-(D-2-phenyl-glycinamido)-3-(1-methyl-1H-tetrazol-5-ylthiomethyl)-3-cephem-4-carboxylic acid (2.5 g) and bis(trimethylsilyl)acetamide (5 ml) in methylene chloride (100 ml) was added at −20° C. to the reaction mixture containing 2-(4-thioxo-6-methyl-4H-pyran-3-yloxy)acetic isobutyloxycarboxylic anhydride. The mixture was stirred up to room temperature for an hour and the solvent was distilled off. The residue was dissolved in a mixture of ethyl acetate, water and 10% hydrochloric acid, whereby the solution was adjusted to pH 1.

An insoluble substance was filtered off and the ethyl acetate layer was washed with an aqueous solution saturated with sodium chloride and dried. After removal of the solvent, the residue was pulverized with diethyl ether and the resulting powder was collected by filtration and dried. Thus obtained crystals (1.6 g) were dissolved in a mixture of ethyl acetate (100 ml) and water (50 ml) and the solution was adjusted to pH 6 to 7 with a sodium bicarbonate aqueous solution. The aqueous layer was washed with ethyl acetate, and ethyl acetate (100 ml) was added to the aqueous layer, after which it was adjusted to pH 1 to 2 with 10% hydrochloric acid. The ethyl acetate layer was washed with an aqueous solution saturated with sodium chloride, dried and treated with active charcoal. The solvent was distilled off to give powder (480 mg) of 7-{D-2-[2-(4-thioxo-6-methyl-4H-pyran-3-yloxy)acetamido]-2-phenylacetamido}-3-(1-methyl-1H-tetrazol-5-ylthiomethyl)-3-cephem-4-carboxylic acid, mp 145° to 150° C. (dec).

N.M.R. Spectrum (Acetone-$D_6$+$D_2O$, δ) Internal standard : Trimethylsilan ppm 2.35 (3H, s), 4.00 (3H, s), 4.38 (2H, s), 4.65 (2H, s), 5.10 (1H, d, J=5 Hz), 5.80 (1H, d, J=5 Hz), 5.75 (1H, s), 7.20 (1H, s), 7.30 to 7.70 (5H, m), 8.24 (1H, s).

(41) A mixture of dimethylformamide (1.03 g) and thionyl chloride (2.48 g) was stirred for 30 minutes at 50° C. and the excess of thionyl chloride was vacuum distilled off. The residue was suspended in methylene chloride (70 ml), and 2-(5-amino-1H-tetrazol-1-yl)acetic acid (1.0 g) was added to the suspension. Dimethylformamide (7 ml) was added thereto and the resultant mixture was stirred at −10° to −15° C. To the resultant solution cooled at −30° C. which contained 2-[5-(N',N'-dimethylaminomethyleneamino)-1H-tetrazol-1-yl]acetyl chloride, was added a solution of 7-(D-2-phenylglycinamido)-3-(1-methyl-1H-tetrazol-5-ylthiomethyl)-3-cephem-4-carboxylic acid (3.23 g) and bis(-trimethylsilyl)acetamide (7.0 g) in methylene chloride (70 ml) which was cooled at −20° C. The resultant mixture was stirred at −20° to −10° C. for 2 hours and at 0° C. for 30 minutes. After removal of the solvent from the reaction mixture, water was added to the residue and the resultant aqueous mixture was stirred, and appearing precipitates were collected by filtration to give powder (2.42 g) of 7-{D-2-[2-(5-(N',N'-dimethylaminomethyleneamino)-1H-tetrazol-1-yl)acetamido]-2-phenylacetamido}-3-(1-methyl-1H-tetrazol-5-ylthiomethyl)-3-cephem-4-carboxylic acid.

N.M.R. Spectrum (DMSO-$D_6$+$D_2O$, δ) Internal standard: Trimethylsilan ppm 2.98 (3H, s), 3.13 (3H, s), 3.60 (2H, s), 3.95 (3H, s), 4.75 (2H, s), 5.00 (1H, d, J=5 Hz), 5.02 (2H, s), 5.65 (1H, d, J=5 Hz), 5.68 (1H, s), 7.3–7.6 (5H, m), 8.45 (1H, s).

(42) A mixture of 7-[D-2-(4-hydroxyphenyl)-glycinamido]-3-(1,3,4-thiadiazol-2-ylthiomethyl)-3-cephem-4-carboxylic acid (2.0 g) and bis(trimethylsilyl)acetamide (8.0 g) in methylene chloride (40 ml) was stirred at 0° C. in an ice-water bath for 10 minutes. To the resultant solution was added 2-(4-oxo-5-chloro-6-methyl-1,4-dihydropyridin-3-yloxy)acetyl chloride (0.945 g), and the mixture was stirred for 4 hours at the same temperature and for 15 minutes with removal of the ice-water bath. The reaction mixture was concentrated, and ethyl acetate and water were added to the residue. The resultant mixture was adjusted to pH 1 with 10% hydrochloric acid. The resulting powder collected by filtration was washed with water, and dissolved in a mixture of an aqueous solution of sodium bicarbonate and water (100 ml). To the resultant solution was added ethyl acetate (100 ml) and the mixture was adjusted to pH 1 to 2 with 10% hydrochloric acid to give powder (1.6 g). The powder was dissolved in an aqueous solution of sodium bicarbonate. The solution was adjusted to pH 7~7.5, and Diaion HP-20 resin (Trade name of the product of Mitsubishi Kasei Co.) (4 ml) were added thereto. The resultant mixture was stirred for 5 minutes and, after removal of the resin, ethyl acetate (80 ml) was added to the aqueous solution. The resultant mixture was adjusted to pH 1 to 2 with 10% hydrochloric acid and the appearing precipitates were collected by filtration to give powder (1.2 g) of 7-{D-2-[2-(4-oxo-5-chloro-6-methyl-1,4-dihydropyridin-3-yloxy)acetamido]-2-(4-hydroxyphenyl)acetamido}-3-(1,3,4-thiadiazol-2-ylthiomethyl)-3-cephem-4-carboxylic acid, m.p. 178° to 180° C. (dec).

N.M.R. Spectrum (Acetone-$D_6$+$D_2O$, δ) Internal standard: Trimethylsilan ppm 2.50 (3H, s), 3.60 and 3.80 (2H, AB$_q$, J=18 Hz), 4.40 and 4.60 (2H, ABg, J=14 Hz), 4.63 (2H, s), 5.13 (1H, d, J=4 Hz), 5.70 (1H, s), 5.83 (1H, d, J=4 Hz), 6.87 (2H, d, J=8 Hz), 7.45 (2H, d, J=8 Hz), 7.77 (1H, s), 9.50 (1H, s).

(43) A mixture of 2-(4-oxo-5-chloro-6-methyl-1,4-dihydropyridin-3-yloxy)acetic acid (2.17 g) and triethylamine (5 ml) in methylene chloride (50 ml) was stirred for 15 minutes. After evaporation to dryness, methylene chloride (50 ml) and then thionyl chloride (1.2 g) were added to the residue under ice-cooling, and the mixture was stirred at the same temperature for 15 minutes and at room temperature for 30 minutes. Precipitated crystals were collected by filtration, washed with methylene chloride and diethyl ether and dried to give powder (2.3 g) of 2-(4-oxo-5-chloro-6-methyl-1,4-dihydropyridin-3-yloxy)acetyl chloride. A solution of 7-[D-2-(4-hydroxyphenyl)glycinamido]-3-carbamoyloxymethyl-3-cephem-4-carboxylic acid (2.1 g) and bis(trimethylsilyl)acetamide (10 ml) in methylene chloride (50 ml) was stirred at 0° C. and the powder (1.2 g) obtained above was added thereto. The reaction mixture was stirred at 0° C. for 2.5 hours and kept in an ice-box over-night. After removal of the solvent, water was added to the residue, and appearing precipitates were collected by filtration, washed with water and dried. The resulting powder (2.5 g) in dry acetone (200 ml) was stirred for 3 hours and collected by filtration, washed with a mixture of acetone and diethyl ether and dried. The resultant powder was dissolved in a mixture of water and an aqueous solution of sodium bicarbonate, whereby the solution was adjusted to pH 7.5, and ethyl acetate (5 ml) was added thereto. To the mixture was added Diaion HP-20 resin (Trade name of the product of Mitsubishi Kasei Co.) (1 ml) and the mixture was stirred for 30 minutes and filtered. The filtrate was adjusted to pH 3 with 10% hydrochloric acid. The resulting crystals were collected by filtration, washed with water, and dissolved in hydrous acetone. The solution was treated with active charcoal (0.3 g), and, after removal of the solvent, the resulting crystals were collected by filtration, washed with water and dried to give crystals (0.85 g) of 7-{D-2-[2-(4-oxo-5-chloro-6-methyl-1,4-dihydropyridin-3-yloxy]acetamido-2-(4-hydroxyphenyl)acetamido}-3-carbamoyloxymethyl-3-cephem-4-carboxylic acid, m.p. 210°–215° C. (dec).

N.M.R. Spectrum (Acetone-$D_6$+$D_2O$, δ) Internal standard: Trimethylsilan ppm 2.22 (3H, s), 3.60 and 3.28 (2H, ABq, J=18 Hz) 4.58 (2H, s), 4.72 and 5.00 (2H, ABq, J=12 Hz), 5.02 (1H, d, J=5 Hz), 5.62 (1H, s), 5.72 (1H, d, J=5 Hz), 6.75 (2H, d, J=8 Hz), 7.38 (2H, d, J=8 Hz), 7.64 (1H, s).

(44) To 2-(4-oxo-5-chloro-6-methyl-1,4-dihydropyridin-3-yloxy)acetic acid (12.1 g) dissolved in a solution of triethylamine (5.55 g) in methylene chloride (240 ml) was dropwise added thionyl chloride (6.61 g) at 0° to 5° C., and the mixture was stirred for an hour at the same temperature. On the other hand, mono(trimethylsilyl)acetamide (80.5 g) was added to a suspension of 7-[D-2-(4-hydroxyphenyl)glycinamido]-3-acetoxymethyl-3-cephem-4-carboxylic acid (23.4 g) in methylene chloride (500 ml), and the mixture was stirred for an hour at 5° to 10° C. to give the solution. This solution was cooled at 0° to 5° C. and added to the solution prepared in the above at once. The resultant mixture was stirred at 2° to 4° C. under ice-cooling for 2.5 hour, and poured into ice-water (800 ml). The mixture was stirred vigorously at 0° to 10° C. for 30 minutes. Precipitates were collected by filtration and dissolved in a solution of sodium bicarbonate (7 g) in water (800 ml). An insolble substance was filtered off. To the filtrate was added ethyl acetate (400 ml), and the mixture was acidified with 10% hydrochloric acid. Precipitates were collected by filtration and dried to give crude product (22.0 g). To the obtained crude product (2.48 g) in a solution of sodium bicarbonate (336 mg) in water (10 ml) was added methanol (70 ml) to give the solution. 1 N Hydrochoride (2 ml) was added thereto and the mixture was heated at 30° to 35° C. Active charcoal (1 g) was added thereto and stirred for 5 minutes. After removal of the charcoal by filtration, 1 N hydrochloric acid (2 ml) was added at 30° C. to the filtrate and the mixture was allowed to stand in a refrigerator for 3 days to give crystals (1.49 g) of 7-{D-2-[2-(4-oxo-5-chloro-6-methyl-1,4-dihydropyridin-3-yloxy)acetamido]-2-(4-hydroxyphenyl)-acetamido}-3-acetoxymethyl-3-cephem-4-carboxylic acid, m.p. 227° to 230° C. (dec).

N.M.R. Spectrum ($CF_3CO_2D$, δ) Internal standard: Trimethylsilan ppm 2.24 (3H, s), 2.80 (3H, s), 3.65 (2H, ABq, J=10 Hz), 5.04 (2H, s), 5.22 (2H, ABq, J=18 Hz), 5.28 (1H, d, J=5 Hz), 5.7 to 6.1 (2H, m), 7.06 (2H, d, J=9 Hz), 7.46 (2H, d, J=9 Hz), 8.25 (1H, s), 7.97 and 8.52 (1H, broad d).

(45) A solution of 2-(4-oxo-5-chloro-6-methyl-1,4-dihydropyridine-3-yloxy)acetic acid (2.18 g), triethylamine (1.01 g) and thionyl chloride (1.19 g) in methylene chloride (40 ml) and a solution of 7-[D-2-(4-hydroxyphenyl)glycinamido]-3-(5-methyl-1,3,4-thiadiazol-2-ylthiomethyl)-3-cephem-4-carboxylic acid (4.93 g) and mono(trimethylsilyl)acetamide (15 g) in methylene chloride (120 ml) were treated in a similar manner to that of the above Example 1-(44) to give crude powder (5.80 g). A solution of thus obtained powder (2.60 g) in a mixture of acetone (50 ml) and water (10 ml) was added under stirring with a solution (6 ml) of sodium 2-ethylhexanoate in n-butanol (4 mmole). The solution was separated by decantation from an oily substance, and 1 N hydrochloric acid (4 ml) was added thereto. After removal of the acetone, water was added to the residue and resultant solid was collected by filtration and pulverized by the addition of acetone (40 ml). The mixture was stirred an hour, the solid was collected by filtration, washed with acetone and dried to give pure crystals (1.82 g) of 7-{D-2-[2-(4-oxo-5-chloro-6-methyl-1,4-dihydropyridin-3-yloxy]acetamido]-2-(4-hydroxyphenyl)acetamido}-3-(5-methyl-1,3,4-thiadiazol-2-ylthiomethyl)-3-cepham-4-carboxylic acid, m.p. 176° to 180° C. (dec).

N.M.R. Spectrum (Acetone-$D_6$+$D_2O$, δ) Internal standard: Trimethylsilan ppm 2.47 (3H, s), 2.70 (3H, s), 3.6 (2H, broad s), 4.4 (2H, ABq, H=14 Hz), 4.57 (2H, s), 5.05 (1H, d, J=5 Hz), 5.67 (1H, s), 5.78 (1H, d, J=5 Hz), 6.80 (2H, d, J=9 Hz), 7.40 (2H, d, J=9 Hz), 7.73(1H, s).

(46) A mixture of 2-(4-oxo-1,4-dihydropyridin-3-yloxy)acetic acid (1.11 g) and triethylamine (1.33 g) in dimethylformamide (20 ml) was heated at 80° C. for 20 minutes under stirring. After the mixture was cooled, methylene chloride (20 ml) and then thionyl chloride (792 mg) were added to the mixture under ice-cooling. The resultant mixture was allowed to stand at room temperature and added at once under stirring at 0° C. to a solution which was prepared by stirring a mixture of 7-[D-2-(4-hydroxyphenyl)glycinamido]-3-(1-methyl-1H-tetrazol-5-ylthiomethyl)-3-cephem-4-carboxylic acid (2.86 g) and mono(trimethylsilyl)acetamide (7 g) in methylene chloride (100 ml) and then cooled at 0° C. The resultant mixture was stirred below 5° C. for 80 minutes and 1 N hydrochloric acid (1 ml) was added thereto. After removal of methylene chloride, ice-water (200 ml) was added to the residue, and the mixture was stirred for 10 minutes under ice-cooling. The resultant precipitates were collected by filtration, washed with ice-water and dissolved in a mixture of a solution of sodium bicarbonate (450 mg) in water (50 ml) and ethyl acetate (40 ml). 1 N hydrochloric acid (10 ml) and further acetone (15 ml) were added to the solution, and the mixture was stirred for 10 minutes and filtered. The aqueous layer of the filtrate was separated, treated with active charcoal (0.5 g), adjusted to pH 3 to 4 with a standard aqueous solution of sodium bicarbonate and cooled. Precipitated crystals were collected by filtration, washed with water and dried to give crystals (1.2 g) of 7-{D-2-[2-(4-oxo-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 177° to 182° C. (dec).

N.M.R. Spectrum (Acetone-$D_6$+DCl, δ) Internal standard: Trimethylsilan ppm 3.70 (2H, s), 4.00 (3H, s), 4.37 (2H, s), 5.05 (2H, s), 5.10 (1H, d, J=5 Hz), 5.73 (1H, s), 5.83 (1H, d, J=5 Hz), 6.86 (2H, d, J=8 Hz), 7.41 (2H, d, J=8 Hz), 7.58 (1H, d, J=6 Hz), 8.50 (1H, d, J=6 Hz), 8.63 (1H, s).

(47) To a solution of 7-[D-2-(4-hydroxyphenyl)-glycinamido]-3-(1-methyl-1H-tetrazol-5-ylthiomethyl)-3-cephem-4-carboxylic acid (2.7 g) and mono(trimethylsilyl)acetamide (6.55 g) in methylene chloride (100 ml) was added dropwise at 3° C. under stirring a solution of 2-(4-oxo-4H-pyran-3-yloxy)acetic acid (850 mg), triethylamine (505 mg) and thionyl chloride (600 mg) in methylene chloride (50 ml), wherein both solutions was prepared in a similar manner to that of Example 1-44). The mixture was stirred at 3° C. for an hour and concentrated. To the residue was added water and the mixture was pulverized under stirring to give precipitate (2.7 g). The precipitates (2.5 g) was dissolved in a solution of sodium bicarbonate (336 mg) in water (15 ml) and subjected to column chromatographyl. The eluate resulting from an eluant, water (200 ml), was adjusted to pH 3 with 10% hydrochloric acid to give pale yellow powder, and the eluate resulting from an eluant, 3% sodium acetate 0.3 hydrate aqueous solution, was adjusted to pH 3 with 10% hydrochloric acid to give pale yellow powder. The above obtained powders were jointed together, washed with water under stirring and dried to give powder (0.9 g) of 7-{D-2-[2-(4-oxo-4H-pyran-3-yloxy)acetamido]-2-(4-hydroxyphenyl)acetamido}-3-(1-methyl-1H-tetrazol-5-ylthiomethyl)-3-cephem-4-carboxylic acid, m.p. 166° to 168° C. (dec).

N.M.R. Spectrum (Acetone-$D_6$+$D_2O$, δ) Internal standard: Trimethylsilan ppm 3.77 (2H, s), 4.07 (3H, s), 4.42 (2H, s), 4.66 (2H, s), 5.15 (1H, d, J=4 Hz), 5.73 (1H, s), 5.86 (1H, d, J=4 Hz), 6.61 (1H, d, J=5 Hz), 6.89 (2H, d, J=9 Hz), 7.46 (2H, d, J=9 Hz), 8.21 (1H, d, J=5 Hz), 8.33 (1H, s).

(48) To a solution of 2-(4-oxo-5-chloro-1,4-dihydropyridin-3-yloxy)acetic acid (2.03 g) in a mixture of triethylamine (2.2 g) in methylene chloride (70 ml) was added with stirring thionyl chloride (1.2 g) with ice-cooling, and the resultant solution was stirred at room temperature for 30 minutes. Thus obtained reaction mixture was added at once under stirring at 10° C. to a solution of 7-[D-2-(4-hydroxyphenyl)glycinamido]-3-(1-methyl-1H-tetrazol-5-ylthiomethyl)-3-cephem-4-carboxylic acid formate (4.3 g) in acetone (70 ml) and a solution of sodium bicarbonate (3.36 g) in water (70 ml), and the resulting mixture was stirred for 30 minutes at 10° C. After removal of the acetone and methylene chloride, the residue was adjusted to pH 3 with 10% hydrochloric acid. Precipitates were collected by filtration, dissolved in an aqueous solution of sodium bicarbonate, adjusted to pH 6.5 and adsorbed on Alumina in a column. The eluate resulting from an eluant, 5% sodium acetate was adjusted to pH 6.5 and the resultant precipitates, were dissolved in an aqueous solution of sodium bicarbonate and reprecipitated by being adjusted to pH 3 with 10% hydrochloric acid to give powder (1.87 g) of 7-{D-2-[2-(4-oxo-5-chloro-1,4-dihydropyridin-3-yloxy)acetamido]-2-(4-hydroxyphenyl)-acetamido}-3-(1-methyl-1H-tetrazol-5-ylthiomethyl)-3-cephem-4-carboxylic acid, m.p. 183° to 185° C. (dec).

N.M.R. Spectrum (CF$_3$COOD) Internal standard: Trimethylsilan ppm 3.79 (2H, broad s), 4.17 (3H, s), 4.56 (2H, ABq, J=14.5 Hz), 5.13 (2H, s), 5.28 (1H, d, J=4 Hz), 5.83 to 6.10 (2H, m), 7.10 (2H, d, J=8 Hz), 7.48 (2H, d, J=8 Hz), 8.46 (1H, s), 8.54 (1H, s).

(49) Similarly, the following compounds were obtained:
(1) 7-[D-2-(2-oxo-3-oxazolidinecarboxamido)-2-(4-hydroxyphenyl)acetamido]-3-(1-methyl-1H-tetrazol-5-ylthiomethyl)-3-cephem-4-carboxylic acid, mp 155° to 160° C. (dec).
(2) 7-{D-2-[2-(4,6-dioxo-3,4,5,6-tetrahydro-2-pyrimidinylthio]acetamido]-2-phenylacetamido}-3-(5-methyl-1,3,4-thiadiazol-5-ylthiomethyl)-3-cephem-4-carboxylic acid, mp 180° to 183° C. (dec).
(3) 7-{D-2-[2-(4H-1,2,4-triazol-3-ylthio)acetamido]-2-phenylacetamido}-3-(5-methyl-1,3,4-thiadiazol-2-ylthiomethyl)-3-cephem-4-carboxylic acid, mp 152° to 154° C. (dec).
(4) 7-{D-2-[2-(4-oxo-5-chloro-6-methyl-1,4-dihydropyridin-3-yloxy)acetamido]-2-(4-hydroxyphenyl)acetamido}-3-(1-carboxymethyl-1H-tetrazol-5-ylthiomethyl)-3-cephem-4-carboxylic acid, m.p. 183° to 185° C. (dec).

EXAMPLE 2

(1) A mixture of thionyl chloride (3.54 g) and dimethylformamide (1.47 g) was stirred for 30 minutes, and after removal of thionyl chloride, the residue was suspended in methylene chloride (100 ml). To the suspension was added at −15° to −10° C. D-2-(2-oxo-3-oxazolidinecarboxamido)-2-(4-hydroxyphenyl)acetic acid (2.8 g) and dimethylformamide (10 ml) and the mixture was stirred for 30 minutes. To this mixture containing D-2-(2-oxo-3-oxazolidinecarboxamido)-2-(4-hydroxyphenyl)acetyl chloride was added a solution of 7-amino-3-(1-methyl-1H-tetrazol-5-ylthiomethyl)-3-cephem-4-carboxylic acid (3.28 g) and trimethylsilylacetamide (10 g) in methylene chloride (100 ml) and the resultant mixture was stirred at −20° C. for 1.5 hours and at −20° to 0° C. for 30 minutes. The reaction mixture was concentrated, and to the residue was added ethyl acetate and water and the mixture was adjusted to pH 1 with 10% hydrochloric acid. The ethyl acetate layer was extracted with an aqueous solution of sodium bicarbonate. The aqueous extract was layered with ethyl acetate and adjusted to pH 3 with 10% hydrochloric acid. The organic layer was separated, washed with water, dried over magnesium sulfate and concentrated. The residue was washed diethyl ether and the resultant powder (2.73 g) was dissolved in acetone and subjected to column chromatography on active charcoal. The eluate was concentrated, and diethyl ether was added to the residue. Precipitates were collected by filtration to give 7-[D-2-(2-oxo-3-oxazolidinecarboxamido)-2-(4-hydroxyphenyl)acetamido]-3-(1-methyl-1H-tetrazol-5-ylthiomethyl)-3-cephem-4-carboxylic acid (1.75 g), mp 155° to 160° C. (dec).

(2) To a solution of D-2-(4-oxo-5-chloro-6-methyl-1,4-dihydropyridin-3-yloxy)acetamido-2-(4-hydroxyphenyl)acetic acid (367 mg) in dimethylformamide (3 ml) was added at −10° C. a solution of triethylamine (1 ml) in methylene chloride. A solution of benzoyl chloride (140 mg) in methylene chloride (about 1 ml) was added at −20° C. thereto. The resultant mixture was stirred at −20° to −30° C. for 40 minutes. To this mixture containing D-2-(4-oxo-5-chloro-6-methyl-1,4-dihydropyridin-3-yloxy)acetamido-2-(4-hydroxyphenyl)acetic benzoyl anhydride, was added uner cooling a solution of 7-amino-3-(1-methyl-1H-tetrazol-5-ylthiomethyl)-3-cephem-4-carboxylic acid (328 mg) and trimethylsilylacetamide (1.05 g) in methylene chloride (10 ml). The mixture was stirred up to room temperature for 2 hours and further at room temperature for an hour and concentrated under vacuum. To the residue was added water (10 ml), 1 N hydrochloric acid (1 ml) and ethyl acetate (30 ml) and the mixture was stirred for 15 minutes. An insoluble substance was filtered off and the aqueous layer was adjusted to pH 3 to 4 with an aqueous solution of sodium bicarbonate. The mixture was kept in an ice-box and a precipitated substance was filtered off. The filtrate was adsorbed on Amberlite XAD-4 (20 ml) (tradename, prepared by Rohm and Haas Co.), washed with water, 1% hydrochloric acid and then with water and eluted with methanol. The methanol eluate was concentrated under vacuum and the residue was dissolved in hydrous acetone. The solution was concentrated under vacuum. The supernatant solution was removed by decantation and the remaining oil was pulverized with a mixture of acetone and diethyl ether to give powder of 7-{D-2-[2-(4-oxo-5-chloro-6-methyl-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, which was identified with the authentic sample with thin-layer chromatography.

(3) Similarly, the following compounds were obtained:
(1) 7-[D-2-(4-hydroxy-3-furazancarboxamido)-2-phenylacetamido]-3-(1-methyl-1H-tetrazol-5-ylthiomethyl)-3-cephem-4-carboxylic acid, mp 133° to 135° C. (dec).
(2) 7{D-2-[3-(2-chlorophenyl)-5-methyl-4-isoxazolecarboxamido]-2-phenylacetamido}-3-(1-methyl-1H-tetrazol-5-ylthiomethyl)-3-cephem-4-carboxylic acid, mp 101° to 103° C. (dec).

(3) 7-[D-2-(2-thenoylamino)-2-phenylacetamido]-3-(1-methyl-1H-tetrazol-5-ylthiomethyl)-3-cephem-4-carboxylic acid, mp 98° to 101° C. (dec).

(4) 7-[D-2-(3-methylthio-5-hydroxy-1,2,4-triazine-6-carboxamido)-2-phenylacetamido]-3-(1-methyl-1H-tetrazol-5-ylthiomethyl)-3-cephem-4-carboxylic acid, mp 178° to 183° C. (dec).

(5) 7-[D-2-(3-mercapto-5-hydroxy-1,2,4-triazine-6-carboxamido)-2-phenylacetamido]-3-(1-methyl-1H-tetrazol-5-ylthiomethyl)-3-cephem-4-carboxylic acid, mp 175° to 179° C. (dec).

(6) 7-[D-2-(4-oxo-4H-pyrido[1,2-a]pyrimidine-3-carboxamido)-2-phenylacetamido]-3-(1-methyl-1H-tetrazol-5-ylthiomethyl)-3-cephem-4-carboxylic acid, mp 103° to 105° C. (dec).

(7) 7-{D-2-[2-(5-methyl-1,3,4-thiadiazol-2-yloxy)acetamido]-2-phenylacetamido}-3-(1-methyl-1H-tetrazol-5-ylthiomethyl)-3-cephem-4-carboxylic acid, mp 175° to 178° C. (dec).

(8) 7-{D-2-[2-(4-oxo-6-chloromethyl-4H-pyran-3-yloxy)acetamido]-2-phenylacetamido}-3-(1-methyl-1H-tetrazol-5-ylthiomethyl)-3-cephem-4-carboxylic acid, mp 145° to 150° C. (dec).

(9) 7-[D-2-(2-oxo-5-phenyl-3-oxazolidinecarboxamido)-2-phenylacetamido]-3-(1-methyl-1H-tetrazol-5-ylthiomethyl)-3-cephem-4-carboxylic acid, mp 115° to 120° C. (dec).

(10) 7-[D-2-(2-oxo-3-oxazolidinecarboxamido)-2-phenylacetamido]-3-(1-methyl-1H-tetrazol-5-ylthiomethyl)-3-cephem-4-carboxylic acid, mp 165° to 170° C. (dec).

(11) 7-[D-2-(3-oxo-2-isoxazolidinecarboxamido)-2-phenylacetamido]-3-(1-methyl-1H-tetrazol-5-ylthiomethyl)-3-cephem-4-carboxylic acid, mp 138° to 144° C. (dec).

(12) 7-[D-2-(2-oxo-3-thiazolidinecarboxamido)-2-phenylacetamido]-3-(1-methyl-1H-tetrazol-5-ylthiomethyl)-3-cephem-4-carboxylic acid, mp 143° to 148° C. (dec).

(13) 7-[D-2-(3-oxo-4-thiomorpholinecarboxamido)-2-phenylacetamido]-3-(1-methyl-1H-tetrazol-5-ylthiomethyl)-3-cephem-4-carboxylic acid, mp 151° to 155° C.

(14) 7-[D-2-(2-methylthio-5-oxo-5,6-dihydro-4H-1,3,4-thiadiazine-4-carboxamido)-2-phenylacetamido]-3-(1-methyl-1H-tetrazol-5-ylthiomethyl)-3-cephem-4-carboxylic acid, mp 128° to 134° C. (dec).

(15) 7-[D-2-(2-oxo-5-methylthio-2,3-dihydro-1,3,4-thiadiazolecarboxamido)-2-phenylacetamido]-3-(1-methyl-1H-tetrazol-5-ylthiomethyl)-3-cephem-4-carboxylic acid, mp 146° to 150° C.

(16) 7-[D-2-(2-imino-4-oxo-1,2,3,4-tetrahydropyrimidin-6-ylacetamido)-2-phenylacetamido]-3-(1-methyl-1H-tetrazol-5-ylthiomethyl)-3-cephem-4-carboxylic acid, mp 200° to 205° C. (dec).

(17) 7-[D-2-(2-oxo-5-methyl-2,3-dihydro-1,3,4-oxadiazole-3-carboxamido)-2-phenylacetamido]-3-(1-methyl-1H-tetrazol-5-ylthiomethyl)-3-cephem-4-carboxylic acid, mp 145° to 150° C. (dec).

(18) 7-[D-2-(1-phenyl-5-oxo-4,5-dihydro-1H-1,2,3-triazole-4-carboxamido)-2-phenylacetamido]-3-(1-methyl-1H-tetrazol-5-ylthiomethyl)-3-cephem-4-carboxylic acid, mp 180° to 192° C. (dec).

(19) 7-{D-2-[2-(2-pyridyloxy)acetamido]-2-phenylacetamido}-3-(1-methyl-1H-tetrazol-5-ylthiomethyl)-3-cephem-4-carboxylic acid, mp 127° to 132° C. (dec).

(20) 7-[D-2-(3-oxo-6-chloro-2,3-dihydro-4-pyridazinecarboxamido)-2-phenylacetamido]-3-(1-methyl-1H-tetrazol-5-ylthiomethyl)-3-cephem-4-carboxylic acid, mp 153° to 155° C. (dec).

(21) 7-[D-2-(2,4-dioxo-1,2,3,4-tetrahydro-6-pyrimidinecarboxamido)-2-phenylacetamido]-3-(5-methyl-1,3,4-thiadiazol-2-ylthiomethyl)-3-cephem-4-carboxylic acid, mp 195° to 200° C. (dec).

(22) 7-{D-2-[2-(2-pyridyloxy)acetamido]-2-phenylacetamido}-3-methyl-3-cephem-4-carboxylic acid, mp 209° to 211° C. (dec).

(23) Sodium 7-[D-2-(2-phthalimidoacetamido)-2-phenylacetamido]-3-(5-methyl-1,3,4-thiadiazol-2-ylthiomethyl)-3-cephem-4-carboxylate, mp 160° to 170° C. (dec).

(24) 7-{D-2-[2-(2-amino-4-thiazolyl)acetamido]-2-phenylacetamido}-3-(1-methyl-1H-tetrazol-5-ylthiomethyl)-3-cephem-4-carboxylic acid, mp 185° to 190° C. (dec).

(25) 7-[D-2-(2-amino-4-thiazolecarboxamido)-2-phenylacetamido]-3-(1-methyl-1H-tetrazol-5-ylthiomethyl)-3-cephem-4-carboxylic acid, mp 185° to 190° C. (dec).

(26) 7-[D-2-(3-carboxy-2-pyrazinecarboxamido)-2-phenylacetamido]-3-(5-methyl-1,3,4-thiadiazol-2-ylthiomethyl)-3-cephem-4-carboxylic acid, mp 167° to 170° C. (dec).

(27) 7-{D-2-[2-(3-methyl-5-oxo-4,5-dihydro-1H-1,2,4-triazol-4-yl)acetamido]-2-phenylacetamido}-3-(1-methyl-1H-tetrazol-5-ylthiomethyl)-3-cephem-4-carboxylic acid, mp 168° to 175° C. (dec).

(28) 7-{D-2-[2-(2-thioxo-4-methyl-2,3-dihydro-3-thiazolyl)acetamido]-2-phenylacetamido}-3-(1-methyl-1H-tetrazol-5-ylthiomethyl)-3-cephem-4-carboxylic acid, mp 150° to 155° C. (dec).

(29) 7-{D-2-[2-(3-hydroxy-6-oxo-1,6-dihydro-1-pyridazinyl)acetamido]-2-phenylacetamido}-3-(1-methyl-1H-tetrazol-5-ylthiomethyl)-3-cephem-4-carboxylic acid, mp 168° to 171° C. (dec).

(30) 7-{D-2-[2-(1,6-dimethyl-4-oxo-1,4-dihydropyridin-3-yloxy)acetamido]-2-phenylacetamido}-3-(1-methyl-1H-tetrazol-5-ylthiomethyl)-3-cephem-4-carboxylic acid, mp 168° to 173° C. (dec).

(31) Sodium 7-{D-2-[2-(4-oxo-5-chloro-6-methyl-1,4-dihydropyridin-3-yloxy)acetamido]-2-phenylacetamido}-3-(1-methyl-1H-tetrazol-5-ylthiomethyl)-3-cephem-4-carboxylate, mp 180° to 185° C. (dec).

(32) 7-(D-2-nicotinamido-2-phenylacetamido)-3-methyl-3-cephem-4-carboxylic acid, mp 183° to 185° C. (dec).

(33) 7-(D-2-picolinamido-2-phenylacetamido)-3-methyl-3-cephem-4-carboxylic acid, mp 150° to 160° C. (dec).

(34) 7-{D-2-[2-(4,6-dioxo-3,4,5,6-tetrahydro-2-pyrimidin-ylthio)acetamido]-2-phenylacetamido}-3-(5-methyl-1,3,4-thiadiazol-2-ylthiomethyl)-3-cephem-4-carboxylic acid, mp 180° to 183° C. (dec).

(35) 7-{D-2-[2-(4H-1,2,4-triazol-3-ylthio)acetamido]-2-phenylacetamido}-3-(5-methyl-1,3,4-thiadiazol-2-ylthiomethyl)-3-cephem-4-carboxylic acid, mp 152° to 154° C. (dec).

(36) 7-{D-2-[2-(4-oxo-5-chloro-6-hydroxymethyl-1,4-dihydropyridin-3-yloxy)acetamido]-2-phenylacetamido}-3-(1-methyl-1H-tetrazol-5-ylthiomethyl)-3-cephem-4-carboxylic acid, mp 175° to 180° C. (dec).

(37) 7-{D-2-[2-(4-oxo-6-chloromethyl-1,4-dihydropyridin-3-yloxy)acetamido]-2-phenylacetamido}-3-(1-methyl-1H-tetrazol-5-ylthiomethyl)-3-cephem-4-carboxylic acid, mp 165° to 170° C. (dec).

(38) 7-{D-2-[2-(4-oxo-6-methyl-1,4-dihydropyridin-3-yloxy)acetamido]-2-phenylacetamido}-3-(1-methyl-1H-tetrazol-5-ylthiomethyl)-3-cephem-4-carboxylic acid, mp 170° to 175° C. (dec).

(39) 7-{D-2-[2-(4-oxo-1,4-dihydropyrimidin-5-yloxy)acetamido]phenylacetamido}-3-(1-methyl-1H-tetrazol-5-ylthiomethyl)-3-cephem-4-carboxylic acid, mp 170° to 175° C. (dec).

(40) 7-{D-2-[2-(2-oxo-1,2-dihydropyrazin-1-yloxy)acetamido]-2-phenylacetamido}-3-(1-methyl-1H-tetrazol-5-ylthiomethyl)-3-cephem-4-carboxylic acid, mp 120° to 125° C. (dec).

(41) 7-{D-2-[2-(4-thioxo-6-methyl-4H-pyran-3-yloxy)acetamido]-2-phenylacetamido}-3-(1-methyl-1H-tetrazol-5-ylthiomethyl)-3-cephem-4-carboxylic acid, mp 145° to 150° C. (dec).

(42) 7-{D-2-[2-(5-(N',N'-dimethylaminomethyleneamino)-1H-tetrazol-1-yl)acetamido]-2-phenylacetamido}-3-(1-methyl-1H-tetrazol-5-ylthiomethyl)-3-cephem-4-carboxylic acid.

N.M.R. Spectrum (DMSO-$D_6$+$D_2O$, δ) Internal standard: Trimethylsilan ppm 2.98 (3H, s), 3.13 (3H, s), 3.60 (2H, s), 3.95 (3H, s), 4.75 (2H, s), 5.00 (1H, d, J=5 Hz), 5.02 (2H, s), 5.65 (1H, d, J=5 Hz), 5.68 (1H, s), 7.3–7.6 (5H, m), 8.45 (1H, s).

(43) 7-{D-2-[2-(4-oxo-5-chloro-6-metyl-1,4-dihydropyridin-3-yloxy)acetamido]-2-(4-hydroxyphenyl)acetamido}-3-(1,3,4-thiadiazol-2-ylthiomethyl)-3-cephem-4-carboxylic acid, mp 178° to 180° C. (dec).

(44) 7-{D-2-[2-(4-oxo-5-chloro-6-methyl-1,4-dihydropyridin-3-yloxy]acetamido-2-(4-hydroxyphenyl)acetamido}-3-carbamoyloxymethyl-3-cephem-4-carboxylic acid, mp 210° to 215° C. (dec).

(45) 7-{D-2-[2-(4-oxo-5-chloro-6-methyl-1,4-dihydropyridin-3-yloxy)acetamido]-2-(4-hydroxyphenyl)acetamido}-3-acetoxymethyl-3-cephem-4-carboxylic acid, m.p. 227° to 230° C. (dec).

(46) 7-{D-2-[2-(4-oxo-5-chloro-6-methyl-1,4-dihydropyridin-3-yloxy)acetamido]-2-(4-hydroxyphenyl)acetamido}-3-(5-methyl-1,3,4-thiadiazol-2-ylthiomethyl)-3-cephem-4-carboxylic acid, m.p. 176° to 180° C. (dec).

(47) 7-{D-2-[2-(4-oxo-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 177° to 182° C. (dec).

(48) 7-{D-2-[2-(4-oxo-4H-pyran-3-yloxy)acetamido]-2-(4-hydroxyphenyl)acetamido}-3-(1-methyl-1H-tetrazol-5-yl-thiomethyl)-3-cephem-4-carboxylic acid, m.p. 166° to 168° C. (dec).

(49) 7-{D-2-[2-(4-oxo-5-chloro-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 183° to 185° C. (dec).

(50) 7-{D-2-[2-(4-oxo-5-chloro-6-methyl-1,4-dihydropyridin-3-yloxy)acetamido]-2-(4-hydroxyphenyl)acetamido}-3-(1-carboxymethyl-1H-tetrazol-5-ylthiomethyl)-3-cephem-4-carboxylic acid, m.p. 183° to 185° C. (dec).

EXAMPLE 3

(1) To a solution of 7-{D-2-[2-(4-oxo-5-chloro-6-methyl-1,4-dihydropyridin-3-yloxy)acetamido]-2-(4-hydroxyphenyl)acetamido}-3-acetoxymethyl-3-cephem-4-carboxylic acid (6.20 g) in phosphoric acid buffer solution (pH 6.4, 250 ml) were added sodium bicarbonate (0.84 g) and then disodium 2-(5-mercapto-1H-tetrazol-1-yl)acetate (2.65 g). The mixture was stirred for 4.5 hours at 65° C. in a stream of $N_2$ gas and cooled. An insoluble substance was filtered off. To the filtrate was layered ethyl acetate (200 ml) and adjusted to pH 2 to 3 with 10% hydrochloric acid under ice-cooling. The resulting precipitates were collected by filtration and washed with ethyl acetate to give crude product (3.93 g). The mixture of thus obtained crude product (2.0 g) and sodium bicarbonate (234 mg) in water (6 ml) was adjusted to pH 5.6 to 5.8 with phosphoric acid buffer solution (pH 6.4, about 40 ml), and then passed through Karamuraito (Trade name of ion-exchange resin produced by Fuji Kagakukogyo, 10.0 g). The eluate (200 ml) resulting from an eluant, water, was adjusted to pH 1 to 2 with 10% hydrochloric acid, and the precipitates were collected by filtration, washed with water and dried to give powder (1.35 g) of 7-{D-2-[2-(4-oxo-5-chloro-6-methyl-1,4-dihydropyridin-3-yloxy)acetamido]-2-(4-hydroxyphenyl)acetamido}-3-(1-carboxymethyl-1H-tetrazol-5-ylthiomethyl)-3-cephem-4-carboxylic acid, m.p. 183° to 185° C. (dec).

N.M.R. Spectrum (Acetone-$D_6$+$D_2O$, δ) Internal standard: Trimethylsilan ppm 2.50(3H,s), 3.7(2H, broad s), 4.66(2H, s), 5.12(1H, d, J=5 Hz), 5.32(2H, s), 5.72(1H, s), 5.85(1H, d, J=5 Hz), 6.88(2H, d, J=10 Hz), 7.45(2H, d, J=10 Hz, 7.78(1H, s).

(2) Similarly, the following compounds were obtained:

(1) 7-[D-2-(4-hydroxy-3-furazancarboxamido)-2-phenylacetamido]-3-(1-methyl-1H-tetrazol-5-ylthiomethyl)-3-cephem-4-carboxylic acid, mp 133° to 135° C. (dec).

(2) 7-{D-2-[3-(2-chlorophenyl)-5-methyl-4-isoxazole carboxamido]-2-phenylacetamido}-3-(1-methyl-1H-tetrazol-5-ylthiomethyl)-3-cephem-4-carboxylic acid, mp 101° to 103° C. (dec).

(3) 7-[D-2-(2-thenoylamino)-2-phenylacetamido]-3-(1-methyl-1H-tetrazol-5-ylthiomethyl)-3-cephem-4-carboxylic acid, mp 98° to 101° C. (dec).

(4) 7-[D-2-(3-methylthio-5-hydroxy-1,2,4-triazine-6-carboxamido)-2-phenylacetamido]-3-(1-methyl-1H-tetrazol-5-ylthiomethyl)-3-cephem-4-carboxylic acid, mp 178° to 183° C. (dec).

(5) 7-[D-2-(3-mercapto-5-hydroxy-1,2,4-triazine-6-carboxamido)-2-phenylacetamido]-3-(1-methyl-1H-tetrazol-5-ylthiomethyl)-3-cephem-4-carboxylic acid, mp 175° to 179° C. (dec).

(6) 7-[D-2-(4-oxo-4H-pyrido[1,2-a]pyrimidine-3-carboxamido)-2-phenylacetamido]-3-(1-methyl-1H-tetrazol-5-ylthiomethyl)-3-cephem-4-carboxylic acid, mp 103° to 105° C. (dec).

(7) 7-{D-2-[2-(5-methyl-1,3,4-thiadiazol-2-yloxy)acetamido]-2-phenylacetamido}-3-(1-methyl-1H-tetrazol-5-ylthiomethyl)-3-cephem-4-carboxylic acid, mp 175° to 178° C. (dec).

(8) 7-[D-2-(2-imino-4-oxo-1,2,3,4-tetrahydropyrimidin-4-ylacetamido)-2-phenylacetamido]-3-(1-methyl-1H-tetrazol-5-ylthiomethyl)-3-cephem-4-carboxylic acid, mp 200° to 205° C. (dec).

(9) 7-[D-2-(1-phenyl-5-oxo-4,5-dihydro-1H-1,2,3-triazole-4-carboxamido)-2-phenylacetamido]-3-(1-methyl-1H-tetrazol-5-ylthiomethyl)-3-cephem-4-carboxylic acid, mp 180° to 192° C. (dec).

(10) 7-{D-2-[2-(2-pyridyloxy)acetamido]-2-phenylacetamido}-3-(1-methyl-1H-tetrazol-5-ylthiomethyl)-3-cephem-4-carboxylic acid, mp 127° to 132° C. (dec).

(11) 7-[D-2-(3-oxo-6-chloro-2,3-dihydro-4-pyridazinecarboxamido)-2-phenylacetamido]-3-(1-methyl-1H-tetrazol-5-ylthiomethyl)-3-cephem-4-carboxylic acid, mp 153° to 155° C. (dec).

(12) 7-[D-2-(2,4-dioxo-1,2,3,4-tetrahydro-6-pyrimidinecarboxamido)-2-phenylactamido]-3-(5-methyl-1,3,4-thiadiazol-2-ylthiomethyl)-3-cephem-4-carboxylic acid, mp 195° to 200° C. (dec).

(13) Sodium 7-[D-2-(2-phthalimidoacetamido)-2-phenylacetamido]-3-(5-methyl-1,3,4-thiadiazol-2-ylthiomethyl)-3-cephem-4-carboxylate, mp 160° to 170° C. (dec).

(14) 7-{D-2-[2-(2-amino-4-thiazolyl)acetamido]-2-phenylacetamido}-3-(1-methyl-1H-tetrazol-5-ylthiomethyl)-3-cephem-4-carboxylic acid, mp 185° to 190° C. (dec).

(15) 7-[D-2-(2-amino-4-thiazolecarboxamido)-2-phenylacetamido]-3-(1-methyl-1H-tetrazol-5-ylthiomethyl)-3-cephem-4-carboxylic acid, mp 185° to 190° C. (dec).

(16) 7-[D-2-(3-carboxy-2-pyrazinecarboxamido)-2phenylacetamido]-3-(5-methyl-1,3,4-thiadiazol-2-ylthiomethyl)-3-cephem-4-carboxylic acid, mp 167° to 170° C. (dec).

(17) 7-{D-2-[2-(3-methyl-5-oxo-4,5-dihydro-1H-1,2,4-triazol-4-yl)acetamido]-2-phenylacetamido}-3-(1-methyl-1H-tetrazol-5-ylthiomethyl)-3-cephem-4-carboxylic acid, mp 168° to 175° C. (dec).

(18) 7-{D-2-[2-(2-thioxo-4-methyl-2,3-dihydro-3-thiazolyl)acetamido]-2-phenylacetamido}-3-(1-methyl-1H-tetrazol-5-ylthiomethyl)-3-cephem-4-carboxylic acid, mp 150° to 155° C. (dec).

(19) 7-{D-2-[2-(3-hydroxy-6-oxo-1,6-dihydro-1-pyridazinyl)acetamido]-2-phenylacetamido}-3-(1-methyl-1H-tetrazol-5-ylthiomethyl)-3-cephem-4-carboxylic acid, mp 168° to 171° C. (dec).

(20) 7-{D-2-[2-(1,6-dimethyl-4-oxo-1,4-dihydropyridin-3-yloxy)acetamido]-2-phenylacetamido}-3-(1-methyl-1H-tetrazol-5-ylthiomethyl)-3-cephem-4-carboxylic acid, mp 168° to 173° C. (dec).

(21) Sodium 7-{D-2-[2-(4-oxo-5-chloro-6-methyl-1,4-dihydropyridin-3-yloxy)acetamido]-2-phenylacetamido}-3-(1-methyl-1H-tetrazol-5-ylthiomethyl)-3-cephem-4-carboxylate, mp 180° to 185° C. (dec).

(22) 7-{D-2-[2-(4,6-dioxo-3,4,5,6-tetrahydro-2-pyrimidinylthio)acetamido]-2-phenylacetamido}-3-(5-methyl-1,3,4-thiadiazol-2-ylthiomethyl)-3-cephem-4-carboxylic acid, mp 180° to 183° C. (dec).

(23) 7-{D-2-[2-(4H-1,2,4-triazol-3-ylthio)acetamido]-2-phenylacetamido}-3-(5-methyl-1,3,4-thiadiazol-2-ylthiomethyl)-3-cephem-4-carboxylic acid, mp 152° to 154° C. (dec).

(24) 7-{D-B 2-[2-(4-oxo-5-chloro-6-hydroxymethyl-1,4-dihydropyridin-3-yloxy)acetamido]-2-phenylacetamido}-3-(1-methyl-1H-tetrazol-5-ylthiomethyl)-3-cephem-4-carboxylic acid, mp 175° to 180° C. (dec).

(25) 7-{D-2-[2-(4-oxo-6-methyl-1,4-dihydropyridin-3-yloxy)acetamido]-2-phenylacetamido}-3-(1-methyl-1H-tetrazol-5-ylthiomethyl)-3-cephem-4-carboxylic acid, mp 170° to 175° C. (dec).

(26) 7-{D-2-[2-(4-oxo-1,4-dihydropyrimidin-5-yloxy)acetamido]phenylacetamido}-3-(1-methyl-1H-tetrazol-5-ylthiomethyl)-3-cephem-4-carboxylic acid, mp 170° to 175° C. (dec).

(27) 7-{D-2-[2-(2-oxo-1,2-dihydropyrazin-1-yloxy)acetamido]-2-phenylacetamido}-3-(1-methyl-1H-tetrazol-5-ylthiomethyl)-3-cephem-4-carboxylic acid, mp 120° to 125° C. (dec).

(28) 7-{D-2-[2-(4-thioxo-6-methyl-4H-pyran-3-yloxy)acetamido]-2-phenylacetamido}-3-(1-methyl-1H-tetrazol-5-ylthiomethyl) -3-cephem-4-carboxylic acid, mp 145° to 150° C. (dec).

(29) 7-{D-2-[2-(4-oxo-5-chloro-6-metyl-1,4-dihydropyridin-3-yloxy)actamido]-2-(4-hydroxyphenyl)acetamido}-3-(1,3,4-thiadiazol-2-ylthiomethyl)-3-cephem-4-carboxylic acid, mp 178° to 180° C. (dec).

(30) 7-{D-2-[2-(4-oxo-5-chloro-6-methyl-1,4-dihydropyridin-3-yloxy)acetamido]-2-(4-hydroxyphenyl)acetamido}-3-(5-methyl-1,3,4-thiadiazol-2-ylthiomethyl)-3-cephem-4-carboxylic acid, m.p. 176° to 180° C. (dec).

(31) 7-{D-2-[2-(4-oxo-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 177° to 182° C. (dec).

(32) 7-{D-2-[2-(4-oxo-4H-pyran-3-yloxy)acetamido]-2-(4-hydroxyphenyl)acetamido}-3-(1-methyl-1H-tetrazol-5-ylthiomethyl)-3-cephem-4-carboxylic acid, m.p. 166° to 168° C. (dec).

(33) 7-{D-2-[2-(4-oxo-5-chloro-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 183° to 185° C. (dec).

(34) 7-{D-2-[2-(4-oxo-5-chloro-6-methyl-1,4-dihydropyridin-3-yloxy)acetamido]-2-(4-hydroxyphenyl)acetamido}-3-(1-methyl-1H-tetrazol-5-ylthiomethyl)-3-cephem-4-carboxylic acid, m.p. 180° to 185° C. (dec).

(35) 7-{D-2-[2-(5-amino-1H-tetrazol-1-yl)acetamido]-2-phenylacetamido}-3-(1-methyl-1H-tetrazol-5-ylthiomethyl)-3-cephem-4-carboxylic acid, m.p. 160.5° to 164° C. (dec).

EXAMPLE 4

(1) 7-(D-2-Phenylglycinamido)-3-(2-methy-1,3,4-thiadiazol-5-ylthiomethyl)-3-cephem-4-carboxylic acid formate (6.3 g) and bis(trimethylsilyl)acetamide (12 g) was dissolved in methylene chloride (120 ml) under ice-cooling. To the solution was added 2-bromoacetyl bromide (17.4 g) dropwise under ice-cooling. The resultant mixture was stirred at room temperature for an hour and concentrated. To the residue was added ethyl acetate and an aqueous solution of hydrochloric acid, and the mixture was stirred. Precipitates were collected by filtration to give 7-[D-2-(2-bromoacetamido)-2-phenylacetamido]-3-(5-methyl-1,3,4-thiadiazol-2-ylthiomethyl)-3-cephem-4-carboxylic acid (4.40 g). To a mixture of the above obtained bromo-compound (1.98 g) and 2-thioxo-4,6-dioxo-1,2,3,4,5,6-hexahydropyrimidine (0.57 g) in water (65 ml), was added N sodium hydroxide (6.6 ml) under ice-cooling, and the resultant mixture was adjusted at room temperature to pH 6.6 to 6.8 with an aqueous solution of sodium bicarbonate which was prepared by sodium bicarbonate (276 mg) and water (5 ml). The resultant mixture was stirred at room temperature for 20 hours and acidified with 10% hydrochloric acid. Precipitates were collected by filtration, and dissolved in aceton containing water and then subjected to column chromatography on active charcoal with an eluent of a mixture of water and acetone. The resultant powder was washed with diethyl ether to give powder (0.45 g) of 7-{D-2-[2-(4,6-dioxo-3,4,5,6-tetrahydro-2-pyrimidinylthio)acetamido]-2-phenylacetamido}-3-(5-methyl-1,3,4-thiadiazol-2-ylthiomethyl)-3-cephem-4-carboxylic acid, mp 180° to 183° C. (dec).

(2) A mixture of D-2-(2-bromoacetamido)-2-phenylacetic acid (6.00 g) and triethylamine (2.2 g) in methylene chloride (100 ml) was cooled at −38° to −40° C. A solution of pivaloyl chloride (2.65 g) in methylene chloride (10 ml) was dropwise added thereto and the resultant mixture was stirred at the same temperature for 50 minutes. On the other hand, a mixture of 7-amino-3-(2-methyl-1,3,4-thiadiazol-5-ylthiomethyl)-3-cephem-4-carboxylic acid (6.9 g) and bis(trimethylsilyl) acetamide (12.5 g) in methylene chloride was stirred at room temperature for 30 minutes and cooled up to −15° to −20° C. Thus obtained solution was added to the above obtained mixture, and the resultant mixture was stirred at −40° to −10° C. for 30 minutes and at room temperature for 1.5 hours, and concentrated. The residue was added with ethyl acetate and water and the resultant mixture was acidified with hydrochloric acid. The ethyl acetate layer was treated further as mentioned later. An insoluble substance was collected by decantation and dissolved in acetone containing a small amount of water and filtered. To the residue was added ethyl acetate and water, and the organic layer was dried over magnesium sulfate and concentrated. The residue was washed with diethyl ether to give powder (1.78 g) of 7-[D-2-(2-bromoacetamido)-2-phenylacetamido]-3-(5-methyl-1,3,4-thiadiazol-2-ylthiomethyl)-3-cephem-4-carboxylic acid. The above obtained ethyl acetate layer was extracted wih an aqueous solution of sodium bicarbonate. The aqueous layer was acidified and extracted with ethyl acetate. The organic layer was washed with water, dried over magnesium sulfate and concentrated. The residue was washed with diethyl ether to give the same product (2.6 g) as obtained above. A mixture of the above obtained bromo-compound (2.1 g) and 3-mercapto-4H-1,2,4-triazole (0.42 g) in water (70 ml) was adjusted to pH 7.0 to 7.2 with N sodium hydroxide (7 ml) under stirring. The resultant mixture was stirred at room temperature for 30 minutes and adjusted to pH 2 to 3 with N hydrochloric acid (4 ml). Precipitates were collected by filtration, washed with water, dissolved into 20% aqueous acetone and subjected to column chromatography on active charcoal with an eluent of 20% aqueous acetone. The eluate was concentrated under reduced pressure and the residue was washed with diethyl ether to give powder (950 mg) of 7-{D-2-[2-(4H-1,2,4-triazol-3-ylthio)acetamido]-2-phenylacetamido}-3-(5-methyl-1,3,4-thiadiazol-2-ylthiomethyl)-3-cephem-4-carboxylic acid, mp 152° to 154° C. (dec).

EXAMPLE 5

A mixture of 7-{D-2-[2-(5-(N', N'-dimethylaminomethyleneamino)-1H-tetrazol-1-yl)acetamido]2-phenylacetamido}-3-(1-methyl-1H-tetrazol-5-ylthiomethyl)-3-cephem-4-carboxylic acid (2.42 g) in acetone (80 ml) and 5% hydrochloric acid (40 ml) was heated at 50° C. for 2 hours. After removal of the acetone from the reaction mixture, the residue was washed with water and the resulting crystals (2.0 g) were dissolved in a mixture of acetone and water under heating and the solution was treated with active charcoal (1.0 g). After removal of the acetone, the residual crystals were collected by filtration and washed with water to give crystals (1.55 g) of 7-{D-2-[2-(5-amino-1H-tetrazol-1-yl)acetamido]-2-phenylacetamido}-3-(1-methyl-1H-tetrazol-5-ylthiomethyl)-3-cephem-4-carboxylic acid, mp 160.5° to 164° C. (dec).

N.M.R. Spectrum (DMSO -D$_6$+D$_2$O, δ) Internal standard: Trimethylsilan ppm 3.26 (2H, s), 3.95 (3H, s), 4.20 (2H, s), 4.98 (2H, s), 5.02 (1H, d, J=5 Hz), 5.70 (1H, d, J=5 Hz), 5.72 (1H, s), 7.2–7.7 (5H, m).

What is claimed is:

1. A compound of the formula:

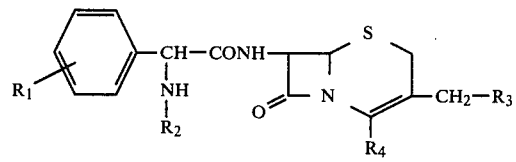

wherein
R$_1$ and R$_3$ are each hydrogen,
R$_2$ is alkanoyl (C$_1$-C$_2$) substituted with pyridyloxy, and
R$_4$ is carboxy
and pharmaceutically acceptable salts thereof.

2. A compound according to claim 1, which is 7-[D-2-[2-(2-pyridyloxy)acetamido]-2-phenylacetamido]-3-methyl-3-cephem-4-carboxylic acid.

3. A compound of the formula:

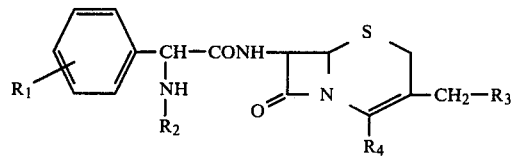

wherein
R$_1$ is hydroxy,
R$_2$ is alkanoyl (C$_1$-C$_2$) substituted with dihydropyridyloxy having oxo, halogen and alkyl (C$_1$-C$_6$),
R$_3$ is alkanoyloxy (C$_1$-C$_6$) or carbamoyloxy, and
R$_4$ is carboxy
and pharmaceutically acceptable salts thereof.

4. A compound according to claim 3, which is 7-[D-2-[2-(4-oxo-5-chloro-6-methyl-1,4-dihydropyridin-3-yloxy)acetamido]-2-(4-hydroxyphenyl)acetamido]-3-acetoxymethyl-3-cephem-4-carboxylic acid.

5. A compound according to claim 3, which is 7-[D-2-[2-(4-oxo-5-chloro-6-methyl-1,4-dihydropyridin-3-yloxy]acetamido-2-(4-hydroxyphenyl)acetamido]-3-carbamoyloxymethyl-3-cephem-4-carboxylic acid.

* * * * *